(12) United States Patent
Baska

(10) Patent No.: US 10,478,576 B2
(45) Date of Patent: Nov. 19, 2019

(54) LARYNGEAL MASK

(71) Applicants: Meenakshi Baska, Strathfield (AU); Kanag Baska, Strathfield (AU)

(72) Inventor: Kanag Baska, Strathfield (AU)

(73) Assignee: Meenakshi Baska, New South Wales (AU)

(*) Notice: Subject to any disclaimer, the term of this patent is extended or adjusted under 35 U.S.C. 154(b) by 565 days.

(21) Appl. No.: 15/125,471

(22) PCT Filed: Mar. 12, 2015

(86) PCT No.: PCT/AU2015/050098
§ 371 (c)(1),
(2) Date: Sep. 12, 2016

(87) PCT Pub. No.: WO2015/135037
PCT Pub. Date: Sep. 17, 2015

(65) Prior Publication Data
US 2017/0216544 A1    Aug. 3, 2017

(30) Foreign Application Priority Data

Mar. 12, 2014  (AU) ................................ 2014900831

(51) Int. Cl.
*A61M 16/04* (2006.01)

(52) U.S. Cl.
CPC ...... *A61M 16/0409* (2014.02); *A61M 16/045* (2014.02); *A61M 16/0415* (2014.02);
(Continued)

(58) Field of Classification Search
CPC ... A01N 25/28; A61M 16/0057; A61M 16/04; A61M 16/0409; A61M 16/0415;
(Continued)

(56) References Cited

U.S. PATENT DOCUMENTS 5,249,571 A * 10/1993 Brain .................... A61M 25/02
                                                              128/200.24
5,303,697 A *  4/1994 Brain .................... A61M 16/04
                                                              128/200.26
(Continued)

FOREIGN PATENT DOCUMENTS

GB       2 111 394 A      7/1983
WO    WO 2005/011784 A1   2/2005
(Continued)

OTHER PUBLICATIONS

Van Zundert et al., "The Baska Mask ® -A new concept in Self-sealing membrane cuff extraglottic airway devices, using a sump and two gastric drains: A critical evaluation", Journal of Obstetric Anaesthesia and Critical Care, 2012, vol. 2, Issue 1, pp. 23-30.
(Continued)

*Primary Examiner* — Annette Dixon
(74) *Attorney, Agent, or Firm* — Fay Sharpe LLP

(57) ABSTRACT

A device for maintaining an airway in a patient includes a mask having a portion that forms a seal with the larynx when the mask is positioned in the laryngo pharynx to thereby prevent ingress of extraneous fluids into the larynx, includes an airway tube connected to or formed with the mask for passing gas to the larynx when the mask is properly inserted into the laryngo pharynx. The mask includes a proximal portion adapted to collapse or compress so that a proximal ventral part of the mask can move relatively towards a dorsal part of the mask during insertion of the mask. This facilitates insertion of the mask into the patient.

19 Claims, 24 Drawing Sheets

(52) U.S. Cl.
CPC .... *A61M 16/0443* (2014.02); *A61M 16/0452* (2014.02); *A61M 16/0484* (2014.02); *A61M 16/0486* (2014.02); *A61M 16/0488* (2013.01)

(58) Field of Classification Search
CPC .......... A61M 16/0425; A61M 16/0434; A61M 16/0443; A61M 16/0463; A61M 16/0488; A61M 16/0493; A61M 16/0616; A61M 16/0825; A61M 2025/022; A61M 2205/0266; A61M 2210/0625; A61M 2230/005; A61M 25/02; B01J 13/16; Y10S 128/26; Y10T 428/2984
See application file for complete search history.

(56) References Cited

U.S. PATENT DOCUMENTS

| | | | | |
|---|---|---|---|---|
| 5,632,271 | A | 5/1997 | Brain | |
| 5,682,880 | A * | 11/1997 | Brain | A61M 16/0488 128/200.26 |
| 9,038,636 | B2 * | 5/2015 | Baska | A61M 16/04 128/207.14 |
| 2004/0139971 | A1 | 7/2004 | Brain | |
| 2006/0180156 | A1 * | 8/2006 | Baska | A61M 16/04 128/207.15 |
| 2013/0220332 | A1 * | 8/2013 | Baska | A61M 16/04 128/207.15 |
| 2013/0269689 | A1 * | 10/2013 | Brain | A61M 16/04 128/200.26 |

FOREIGN PATENT DOCUMENTS

| | | |
|---|---|---|
| WO | WO 2009/026628 A1 | 3/2009 |
| WO | WO 2010/115232 A1 | 10/2010 |
| WO | WO 2011/003135 A1 | 1/2011 |
| WO | WO 2012/024728 A1 | 3/2012 |

OTHER PUBLICATIONS

International Search Report of International Application No. PCT/AU2015/050098, dated Jun. 16, 2015, 8 pages.
Written Opinion of International Application No. PCT/AU2015/050098, dated Jun. 16, 2015, 7 pages.

* cited by examiner

LARYNGEAL MASK

FIELD OF THE INVENTION

The present invention relates to a device for maintaining an airway in a patient. In preferred embodiments, the present invention relates to a laryngeal mask.

BACKGROUND OF THE INVENTION

Maintenance of a viable airway is critical to patient safety during surgical procedures conducted under general anaesthetic. Maintenance of a viable airway during such surgical procedures had, for many years, been achieved by insertion of an endo-tracheal tube into the patient. The endo-tracheal tube was typically inserted through the oral cavity or nasal cavity, into the larynx, through the vocal cords and into the trachea. As the endo-tracheal tube had to be inserted through the vocal cords, difficulty was often experienced in correctly positioning the endo-tracheal tube.

British patent no. 2,111,394 (which corresponds to U.S. Pat. No. 4,509,514) describes a device for maintaining an airway in a patient. The device is described as being an artificial airway device. The device comprises a curved, flexible tube opening at one end into the interior of a hollow mask portion shaped to conform to fit readily into the actual and potential space behind the larynx and to seal around the circumference of the laryngeal inlet without penetrating into the interior of the larynx. Commercial forms of this device have an inflatable collar extending around the periphery of the mask. The inflatable collar is adapted to form the seal around the laryngeal inlet when the collar is inflated. Additionally, the mask portion included an inflatable posterior part which is adapted to press against the back of the throat and thereby increase the sealing pressure around the laryngeal inlet.

British patent no. 2,111,394 states that the shape and (when fitted) the inflatable part or parts of the mask ensure that it approximates closely to the shape of the space between the laryngeal inlet and the walls of the lower part of the throat behind it. Since the walls of tissue forming the back of the throat are relatively rigid, inflation of the mask forces it more tightly against the tissues surrounding the laryngeal inlet, so forming an airtight seal, while tending to anchor the mask in position.

In use of the device described in GB 2,111,394, the device is inserted through the mouth of the patient and down the throat past the epiglottis until the mask comes to rest with its distal end in the base of the throat, lying against the upper end of the normally closed oesophagus. The inflatable ring on the mask is then inflated to seal around the inlet to the larynx. The patient's airway is thus secure and unobstructed and the laryngeal mask can be connected directly to conventional anaesthetic circuit hosing for either positive pressure or spontaneous breathing.

When a patient is placed under general anaesthetic, the patient is frequently lying in the horizontal position on his or her back or side. When under general anaesthetic, reflex response in the body is suppressed and the sphincter closing the top of the stomach from the oesophagus is relaxed. Consequently, gastric juices (which are acidic in nature) can flow along the oesophagus. It is important to ensure that such gastric juices do not enter the trachea as aspiration of gastric juices into the lungs can have potentially fatal consequences.

Similarly, where a patient under general anaesthetic is undergoing a surgical procedure of the nose, mouth or throat (e.g. a tonsillectomy, endoscopic nasal surgery), saliva, blood and nasal secretions can travel down through the laryngo pharynx and into the trachea and thereafter into the lungs. Again, this is a potentially dangerous situation.

When using a laryngeal mask such as the one described in British patent no. 2,111,394, the present inventor has found that if significant volumes of gastric juices collect around the mask the gastric juices can work their way past the seal of the mask and into the larynx. This is dangerous if the gastric juices and acid gets into the lungs.

The laryngeal mask described in British patent no. 2,111,394 may also have problems of leakage occurring in the inflatable ring or collar, due to a faulty valve in the pilot line or due to leakage or tearing of the inflatable ring or collar. It is apparent that deflation of the cuff substantially increases the chance that the seal around the larynx will be lost, which consequently increases the possibility of gastric acids getting into the lungs. Even in normal use without cuff deflation, there remains a possibility that a gush of acid from the stomach can get around the cuff and enter the air passage as there is no other way for the acid to escape (due to the cuff totally blocking the laryngopharynx). The presently available masks also have the limitation that they cannot be used safely on all patients, especially patients with a large abdomen.

In order to minimise the likelihood of the abovementioned problems, the patentee of British patent no. 2,111,394 introduced a laryngeal mask that had a double cuff to produce a total seal around the area of the larynx. This mask also included an additional tube that extends along the back of the laryngeal mask and extends into the oesophagus. This allows gastric acid to be sucked out from the stomach by way of a Ryles tube inserted through this passage. It has been found that applying suction to the oesophageal tube of this laryngeal mask can cause the tissue of the oesophagus to be sucked into the inlet of the second tube. This results in the second tube becoming blocked, thereby preventing removal of gastric acid from the upper oesophagus.

The double cuff laryngeal mask also includes two small additional tubes that open into the larynx-side of the mask. These tubes can be used to remove from the larynx any gastric juices that make their way past the seal into the larynx. However, applying suction to these tubes raises the possibility of removing anaesthetic gases from the trachea and increases the possibility of collapsing the lung or lungs. Successful removal of all the volume of acid coming up from the stomach is also not possible. Consequently, the acid may preferably move into the large diameter airway (trachea) due to the large diameter of the airway providing a path of lower resistance to fluid flow than the smaller diameter opening in the mask and also because the trachea bronchial tube is at a lower level in a supine patient.

The improved laryngeal mask described above is described in Australian patent no. 630433.

In our International patent application no PCT/AU2004/001011, the entire contents of which are herein incorporated by cross reference, we describe a device for maintaining an airway in a patient comprising a mask, the mask having a resilient conformable peripheral portion shaped such that the mask forms a seal with the larynx when the mask is positioned in the laryngo pharynx to thereby prevent ingress of extraneous fluids into the larynx, the peripheral portion of the mask defining at least one cavity for providing fluid communication between the laryngo pharynx and the oesophagus when the mask is inserted into the laryngo pharynx, and an airway tube connected to or formed with the mask for passing gas to the larynx when the mask is properly inserted into the laryngo pharynx.

This device, in preferred embodiments, does not have an inflatable cuff around its periphery. Rather, the walls of the mask are made from a resilient material and the walls themselves comprise a design in which the walls extend outwardly and then upwardly and inwardly. In this fashion, the walls assist in obtaining a seal around the larynx to prevent fluid from the oesophagus entering the larynx during anaesthesia. Further, the mask also has cavities that provide fluid communication between the laryngo pharynx and the oesophagus when the mask is inserted into the laryngo pharynx.

Although laryngeal masks such as the examples described above have found wide acceptance, difficulties can be encountered during insertion of the laryngeal mask into the airway of the patient. In particular, during insertion of the laryngeal masks, the tip of the masks has often been found to come into contact with the pharynx. This necessitates extra manipulation of the mask during insertion in order to properly position the mask in the patient.

The anatomy of the head and neck of humans includes numerous muscles, nerves and cartilages. The thyroid cartilage comprises an open and, generally semi-cylindrical cartilage that extends around the anterior of the upper part of the trachea. Located below the thyroid cartilage is the cricoid cartilage. The cricoid cartilage forms a solid ring of cartilage that extends around the upper part of the trachea. The posterior part of the cricoid cartilage is located in the wall between the trachea and the oesophagus.

The cricoid cartilage, being in the form of a solid ring or closed ring of cartilage, is used to close off the oesophagus in patients who have a possible full stomach and who require emergency surgery or who have stopped breathing. In these instances, either an endotracheal tube or a laryngeal mask is inserted into the patient in order to provide airway ventilation. However, as the patient may have a full stomach, the risk of regurgitation or vomiting is enhanced. Therefore, external cricoid pressure, in which pressure is applied externally from the anterior part of the neck to the cricoid cartilage to compress the oesophagus against the posterior pharyngeal wall, is used to include the upper oesophagus to stop regurgitated material from entering the glottic area to prevent aspiration into the lungs. The external cricoid pressure must be applied and maintained until the time that a viable airway is fully secured. It has been found, in order to successfully apply intermittent positive pressure ventilation (IPPV) using presently available laryngeal masks, external cricoid pressure is necessary. To perform an effective external cricoid pressure requires extra trained personnel.

In our international patent application number PCT/AU2008/001259, the entire contents of which are incorporated herein by cross reference, we describe a device for maintaining an airway in a patient. The device comprises a mask having a peripheral portion that forms a seal with the larynx when the mask is positioned in the laryngo pharynx to thereby prevent ingress of extraneous fluids into the larynx, and an airway tube connected to or formed with the mask for passing gas to the larynx when the mask is properly inserted into the laryngo pharynx. The peripheral portion of the mask includes a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall.

The device described in our international patent application number PCT/AU2008/001259 has been subjected to a number of trials. In an article published in the Journal of Obstetric Anaesthesia and Critical Care, 2012, Volume 2, Issue 1, pages 23 to 30, trials were conducted which evaluated the "first attempt" and "overall insertion" success rates, insertion time, ease of insertion and removal of the device, oropharyngeal leak pressure, and anatomical position at fiberoptic view. The "first attempt" success rate was high (88%) and "overall insertion" success rates was considered "easy" to "very easy" by the operators in 92% of patients. Removal of the device was considered easy in all cases. The oropharyngeal leak pressure was above 30 cm $H_2O$ in all patients and a maximum of 40 cm $H_2O$ was achieved in 82% of the patients.

These results indicate that the mask is easy to insert into a patient and that a strong seal can be formed around the structures of the larynx. As a result, a viable airway can be established by most practitioners using the mask. However, the present inventor has developed modifications to the laryngeal mask to provide an even better success rate for insertion of the mask into a patient to establish a viable airway and to achieve a very high seal pressure of about 50 cm $H_2O$.

BRIEF DESCRIPTION OF THE INVENTION

It is an object of the present invention to provide an improved laryngeal mask that provides for even better insertion than the laryngeal mask described in our international patent application number PCT/AU2008/001259.

In order to clearly describe the present invention, the following conventions for determining directions will be used throughout the specification. It will be understood that, when the airway device is positioned properly in a patient, the mask will have a laryngeal side (which is the side closest to the larynx of the patient, which is also referred to as the ventral side or anterior side of the mask) and the other side, being a dorsal side, that is positioned away from the larynx. The distal end of the dorsal side faces towards the oesophagus. The proximal end of the dorsal side faces towards the oropharynx and mouth of the patient. The side of the mask that faces the larynx and when in use will be referred to throughout this specification as the "laryngeal side" or the "ventral side". In terms of directions, throughout the specification, the term "downwards" or its grammatical equivalents will referred to a direction moving towards the laryngeal or ventral side of the mask. Throughout this specification, the term "upwards" or its grammatical equivalents will referred to a direction moving towards the dorsal side of the mask.

In a first aspect, the present invention provides a device for maintaining an airway in a patient, the device comprising a mask having a portion that forms a seal with the larynx when the mask is positioned in the laryngo pharynx to thereby prevent ingress of extraneous fluids into the larynx, and an airway tube connected to or formed with the mask for passing gas to the larynx when the mask is properly inserted into the laryngo pharynx, wherein the mask includes a proximal portion adapted to collapse or compress so that a proximal ventral part of the mask can move relatively towards a dorsal part of the device during insertion of the mask, or the proximal portion of the ventral side of the mask is of lower profile than the immediately adjacent ventral portions of the mask.

In some embodiments, the device includes a proximal portion adapted to collapse or compress so that a proximal ventral part of the mask can move relatively towards a dorsal part of the mask, such as a proximal dorsal part of the mask, during insertion of the mask. In other embodiments, the device includes a proximal portion of the ventral side of the mask that is of lower profile than the immediately adjacent ventral portions of the mask. In other embodiments, the device includes a proximal portion adapted to collapse or compress so that a proximal ventral part of the mask can move relatively towards a dorsal part of the mask during insertion of the mask and a proximal portion of the ventral side of the mask that is of lower profile than the immediately adjacent ventral portions of the mask.

In embodiments where the device includes a proximal portion of the ventral side of the mask that is of lower profile than the immediately adjacent ventral portions of the mask, the proximal portion of the mask might have the same collapsing or compressing characteristics as the adjacent parts of the mask, or the proximal portion may be adapted to collapse or compress so that a proximal ventral part of the mask can move relatively towards a dorsal part of the mask during insertion of the mask.

The mask must pass between the upper and lower set of teeth in the mouth during the initial part of insertion of the mask into a patient. The gap between the upper and lower set of incisor teeth can vary greatly between different patients. In some patients, this gap can be quite small, due to a number of different reasons, such as the size of a patient's head, the age of the patient, disease in the tempero mandibular joint, infected teeth causing swelling of the jaw, a receded lower jaw, an inability to open the mouth, or dental abscess. On occasions, the patient may not be deeply enough under anaesthetic during induction of anaesthesia, resulting in the anaesthetist not being able to manually open the patient's mouth sufficiently far to insert the laryngeal mask.

The present inventor has found that providing the mask of the present invention with a proximal portion adapted to collapse or compress so that a proximal ventral part of the mask can move relatively towards a dorsal part of the mask allows easier insertion of the mask past the teeth of the patient. Further, the mask is believed to more readily adopt a lowered configuration during insertion, which also allows for easier insertion. In this embodiment, the proximal portion of the mask collapses or compresses more readily than the adjacent portions of the mask.

In some embodiments, the mask includes a chamber having an opening in fluid communication with the airway tube, the chamber including an outlet through which pressurised gases are supplied to the patient. The chamber includes a wall having a wall portion extending from a ventral side of the mask towards a dorsal side of the mask, and the proximal portion of the mask that is adapted to collapse so that a proximal ventral part of the mask can move relatively towards a dorsal part of the mask being located in a proximal region of the wall portion.

Desirably, the wall of the chamber includes a proximal wall portion, opposed side wall portions and a distal portion. The proximal portion of the mask that is adapted to collapse or compress may comprise part of the proximal wall of the chamber. The proximal portion of the mask that is adapted to collapse or compress may extend from the proximal wall portion of the wall of the chamber and at least partly along the opposed side walls of the chamber. In other embodiments, the proximal portion of the mask that is adapted to collapse or compress may be located in only the proximal wall of the chamber. In other embodiments, the proximal portion of the mask that is adapted to collapse or compress may be located in one or both opposed side walls of the chamber, such as in a proximal part of one or both opposed side walls. The portion of the chamber that is adapted to collapse or compress may partially collapse or compress.

In some embodiments, the proximal portion that is adapted to collapse or compress comprises a region having a lesser wall thickness than a wall thickness of adjacent regions.

In some embodiments, the proximal portion that is adapted to collapse or compress comprises a region made from a material of greater flexibility or lesser strength than the immediately adjacent parts of the mask. In one embodiment, the proximal portion may be made from a gel material or a foam material.

In some embodiments, the proximal portion that is adapted to collapse or compress is shaped to facilitate collapsing or compressing. In one embodiment, the proximal portion of the mask, when viewed in cross section, may have a first region extending inwardly into the chamber, a second region depending ventrally from the first region, the second region extending outwardly from the first region, whereby the second region can flex outwardly relative to the first region to thereby facilitate collapsing or compressing.

In another embodiment, the proximal portion that is adapted to collapse or compress comprises the second region extending outwardly and a third region extending ventrally and inwardly from the second region, such the third region can flex inwardly relative to a ventral part of the second region to thereby facilitate collapsing or compressing.

In a further embodiment, the proximal portion is adapted to collapse or compress comprises the first region, second region and third region, as described above.

In some embodiments, the second region includes a part that has a thinner wall section than the first region.

In some embodiments, the first region is provided by a protrusion or projection extending into the chamber, such as in the proximal portion of the chamber. In some embodiments, the second region at least partly defines a recess in the chamber, such as in the proximal portion of the airway chamber. In some embodiments, the third region is at least partly defined by a projection or protrusion extending into the chamber, such as in the proximal portion of the chamber.

In another embodiment, the proximal portion that is adapted to collapse or compress comprises a recess formed in a proximal wall of the mask. In a further embodiment, the proximal portion that is adapted to collapse or compress comprises a region of lower wall thickness in the proximal portion of the mask. In another embodiment, the proximal portion that is adapted to collapse or compress comprises a corrugated region.

In embodiments where the proximal portion of the ventral side of the mask is of lower profile than the immediately adjacent ventral portions of the mask, the ventral portion of the mask may dip towards the dorsal side of the mask in the proximal region thereof.

In some embodiments, the mask includes a proximal portion that is adapted to collapse or compress and a distal portion that is adapted to collapse or compress. The proximal portion may comprise a region having a lesser wall thickness than a wall thickness of adjacent regions and the distal portion may comprise a region having a lesser wall thickness than a wall thickness of adjacent regions. The proximal region may comprise a region of a wall of the chamber and the distal region may comprise a region of a wall of the chamber.

In some embodiments, the proximal portion that is adapted to collapse or compress comprises a proximal region of the mask that is located near a mid-line of the mask, or extends to both sides of a midline of the mask. In some embodiments, the distal portion that is adapted to collapse or compress comprises a distal region of the mask that is located near a mid-line of the mask, or extends to both sides of a midline of the mask.

In some embodiments, the proximal portion that is adapted to collapse or compress may have a wall thickness in the range of from 0.05 mm to 0.5 mm, or from 0.1 mm to 0.4 mm or from 0.1 mm to 0.35 mm. The thickness of the wall may vary from these values, depending upon the material that the mask is made from and the size of the mask.

In some embodiments, the distal portion that is adapted to collapse or compress may have a wall thickness in the range of from 0.05 mm to 0.5 mm, or from 0.1 mm to 0.4 mm or from 0.1 mm to 0.35 mm or from 0.15 to 0.3 mm. The thickness of the wall may vary from these values, depending upon the material that the mask is made from and the size of the mask.

In some embodiments, the mask portion has an airway chamber and the thickness of a side wall of the airway chamber may have a thickness in the range of from 1 mm to 5 mm, or from 2 mm to 4 mm or from 2.4 mm to 3.5 mm. The thickness of the wall may vary from these values, depending upon the material that the mask is made from and the size of the mask.

In some embodiments, the proximal wall portion that is adapted to collapse or compress may have a wall thickness that is from 2% to 20% of the thickness of the side walls adjacent the proximal wall portion, or from 2% to 15% of the thickness of the side walls adjacent the proximal wall portion, or from 2% to 10% of the thickness of the side walls adjacent the proximal wall portion. In some embodiments, the distal wall portion that is adapted to collapse or compress may have a thickness of from 2% to 15% of the thickness of the side walls adjacent the proximal wall portion, or from 5% to 19% of the thickness of the side walls adjacent the proximal wall portion, or from 6% to 8.5% of the thickness of the side walls adjacent the proximal wall portion. The relative thickness of the proximal wall portion and the distal wall portion may vary from those ratios in some embodiments, depending upon the design of the airway chamber, the material used to manufacture the airway device and the size of the mask.

In one embodiment, the mask includes a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall. In this embodiment, the pressurised gas acts to urge the proximal portion of the mask to adopt an extended condition. In other words, the proximal portion of the mask does not stay in a collapsed condition when the mask has been properly inserted into the patient.

In some embodiments, the soft, flexible portion surrounds the outlet of the mask through which gases are supplied to the patient, for example, anaesthetic gas, ventilation for assisted breathing or artificial respiration. As pressurised gases are supplied through the airway tube, the soft, flexible portion expands to come into firmer contact with the tissues surrounding the larynx, thereby forming a better seal around the larynx.

In some embodiments, the device in accordance with the present invention includes a region of relatively higher strength or stiffness extending at least partly around a soft, flexible portion surrounding the outlet of the mask. The region of relatively higher strength or stiffness assists in ensuring that the soft, flexible portion surrounding the outlet of the mask retains its shape during use of the mask. On occasions, some anaesthetists may be inclined to push the distal end of the device quite hard. This can cause the soft, flexible portion surrounding the outlet of the mask to buckle and cause airway obstruction due to loss or restriction of airflow. By providing a region of relatively higher strength or stiffness extending at least partly around the soft flexible portion surrounding the outlet of the mask, the risk that the soft flexible portion will buckle or otherwise go out of shape is reduced.

In some embodiments, the region of relatively higher strength or stiffness extending at least partly around the soft flexible portion surrounding the outlet of the mask comprises a region of relatively high strength or stiffness surrounding the soft flexible portion.

The region of relatively higher strength or stiffness may comprise a region having a larger wall thickness than the wall thickness of the soft flexible portion. The region of relatively higher strength or stiffness may comprise a region including one or more reinforcing means, such as reinforcing ribs, located therein. The region of relatively higher strength or stiffness may comprise a region made from a stiffer material than the material used in the soft flexible portion.

The region of relatively higher strength or stiffness may be at least partly located in a region between the soft, flexible portion surrounding the outlet of the mask and the proximal portion that is adapted to collapse or compress.

In some embodiments, the mask comprises the region of relatively high strength or stiffness, the proximal portion that is adapted to collapse or compress and a dorsal region of relatively high strength or stiffness, the region of relatively high strength or stiffness being continuous with or joining with the dorsal region of relatively high strength or stiffness at a position located distally of a distal part of the proximal portion that is adapted to collapse or compress. In this embodiment, the proximal portion that is adapted to collapse or compress separates part of the region of relatively high strength or stiffness from the dorsal region of relatively high strength or stiffness. As at least part of the region of relatively high strength or stiffness is continuous with or joins with the dorsal region of relatively high strength or stiffness, the part of the region of relatively high strength or stiffness is effectively hinged or sprung from the dorsal region of relatively high strength or thickness. This acts to urge the region of relatively high strength or thickness in a ventral direction when the mask has been inserted into the laryngo pharynx of the patient. This action also acts to extend the proximal portion that is adapted to collapse or compress and this assists in ensuring that the mask adopts an expanded configuration when the mask has been inserted into the laryngo pharynx of the patient. In this manner, the mask tends to adopt its expanded position when it has been properly inserted into the laryngo pharynx of the patient. This assists in maintaining a proper passage for airflow through the mask.

In some embodiments of the present invention, a middle part of the mask is provided with a region of relatively higher strength or stiffness to facilitate pushing of the mask during insertion. This region of relatively higher strength or stiffness stops or minimises the mask collapsing back upon itself from the distal end towards the proximal end during insertion of the mask. It will be appreciated that insertion of the mask requires the anaesthetist to push on the airway tube which, in turn, results in a pushing force being applied to the mask. The region of relatively higher strength or stiffness resists deformation that may otherwise be caused by the pushing force.

The region of relatively higher strength or stiffness may comprise a region located in a middle part of the opposed side walls of the mask. The region of relatively high strength or stiffness may extend from a distal side of a midpoint of each side wall to a proximal side of the midpoint of each side wall. The region of relatively higher strength or stiffness may comprise a region of larger wall thickness.

In one embodiment, the soft, flexible portion has a part that extends inwardly, the inwardly extending portion being located at a ventral side of the mask. The soft flexible portion may have an inner wall that extends towards a dorsal side of the mask. Suitably, the inwardly extending portion or the inner wall includes or defines an opening through which ventilation gases pass. Suitably, the inwardly extending soft, flexible portion (which can be described as a membrane portion) is caused to expand when pressurised ventilation gases are applied to the airway mask. This "inflation" pushes or urges the soft, flexible membrane into firmer contact with the tissues surrounding the laryngeal opening with greater force than is present when pressurised ventilation gases are not applied to the airway mask. As the force with which the soft, flexible membrane is pushed into contact with the tissues surrounding the laryngeal opening is increased by pressurised ventilation gases in the airway tube, the seal achieved by the soft, flexible membrane with the tissues surrounding the laryngeal opening is also improved. Thus, the strength or effectiveness of the soft, flexible membrane in achieving a seal with the tissues surrounding the laryngeal opening is proportional to the pressure of the ventilation gases supplied to the airway tube.

In some embodiments of the present invention, the portion of the soft flexible portion that lies adjacent to the tissues surrounding the larynx is provided with a thicker wall region or is provided with one or more reinforcing ribs. In this embodiment, the risk of this portion of the soft flexible portion of the mask deforming or crinkling during insertion is reduced. This also assists in increasing the rate of successful insertion of the mask into the patient.

The thicker wall region may comprise a region that surrounds the outlet of the mask through which pressurised gases are supplied to the patient. The thicker wall region may comprise a ring surrounding the outlet. The thicker wall region may comprise a horseshoe-shaped or a generally U-shaped region that partly surrounds the outlet of the mask. Alternatively, the thicker wall region may be provided by a plurality of reinforcing ribs. The reinforcing ribs may extend completely around the outlet of the mask. The reinforcing ribs may extend only partly around the outlet of the mask. The reinforcing ribs may comprise one or more horseshoe shaped or a generally U-shaped reinforcing ribs.

In some embodiments, the soft flexible portion lies against and extends along the structures around the larynx when the mask is positioned in the patient, the soft flexible portion being urged or forced into contact with the structures around the larynx when pressurised gas is supplied to the mask.

In some embodiments, the soft flexible portion may include a ventrally extending portion that defines a periphery of the outlet of the mask and a small region that lies adjacent the tissues surrounding the larynx when the mask is positioned in the laryngo pharynx of the patient. In this embodiment, the region of relatively high strength or stiffness may completely surround the soft flexible portion to thereby assist in maintaining the shape of the soft flexible portion.

The soft, flexible membrane may comprise a domed membrane, a folded membrane, or a membrane including a portion that extends substantially parallel to the tissues surrounding the laryngeal opening. The soft, flexible membrane suitably includes or defines an opening, with the soft, flexible membrane desirably having a thin wall thickness in the vicinity of the opening.

The soft, flexible portion may be in the form of a soft flexible membrane. The soft flexible membrane may be integrally formed with the mask. Alternatively, the soft, flexible membrane may be joined to the mask, for example, by use of a suitable adhesive, by ultrasonic welding, or by any other suitable joining technique.

The soft, flexible membrane may form part of a larger structure, with the larger structure having portions or regions of thicker wall thickness or less flexibility than the soft, flexible membrane. The larger structure may be arranged such that the soft, flexible membrane contacts the tissues surrounding the laryngeal opening when the airway device is inserted into a patient. The larger structure may be arranged such that the soft, flexible membrane lies against and substantially parallel to the tissues surrounding the laryngeal opening when the airway device is inserted into a patient.

The soft, flexible membrane may be utilised with any of the airway devices described in with reference to the other aspects of the present invention, as described herein.

When pressurised ventilation gases are supplied to the airway tube, the increased internal pressure within the mask (arising from the pressurised ventilation gases) will cause expansion of the proximal portion that is adapted to collapse or compress, thereby assisting in maintaining the mask in its expanded state, which assists in maintaining an airway for the patient.

In other embodiments of all aspects of the present invention, the mask may be made from a resilient material. When pressurised ventilation gases are supplied to the airway tube, the increased internal pressure within the mask (arising from the pressurised ventilation gases) will cause the mask to circumferentially expand. The mask may be made of varying wall thicknesses and thus its expansion can vary considerably in different parts of the mask. This expansion tends to increase the seal around the mask in all directions against the pharyngeal walls. As the part of the mask facing the anterior pharyngeal wall (i.e. the tissues surrounding the laryngeal opening) is also made with wall regions of varying thicknesses, the thinner parts expand the most and exert further pressure against the tissues that they are in contact with. This expansion of the mask is caused by the ventilation gases. Thus, the strength or effectiveness of the seal achieved by the mask is proportional to the pressure of the ventilation gases used.

In some embodiments, the device of the present invention may further include one or more loops or brackets attached to or extending from the airway tube to enable the device to be more easily taped or tied in place during use in a patient. In one embodiment, the one or more loops or brackets are positioned on a ventral side of the airway tube. In another embodiment, the one or more loops or brackets are positioned on both a ventral side and a dorsal side of the airway tube.

In yet another embodiment, the airway tube may be provided with one or more depressions to facilitate securing of the mask and for positioning of the fingers of a doctor utilising the device. For example, finger grips for two or more fingers may be formed in the airway tube.

The mask of the present invention may be used for positive pressure ventilation, for resuscitation and for use in anaesthesia.

In some embodiments, the mask may be provided with a dorsal groove or recess near the distal tip thereof. This dorsal groove or recess tends to cause the distal tip of the mask to fold under when it contacts the posterior wall of the throat when the mask is being inserted into the patient. As insertion continues, the distal tip eventually unfolds to the correct position. Therefore, the dorsal groove or recess near the distal tip of the mask helps prevent snagging of the mask on the posterior wall of the throat during insertion. It also reduces the likelihood of damage to the mucous membranes and assists in causing the mask to move the right way during insertion into the patient.

In some embodiments, the distal end of the ventral peripheral portion of the mask includes an upwardly extending portion that extends towards the dorsal side of the mask. This is advantageous because, during insertion of the mask, as the distal end of the mask reaches the larynx, the upwardly extending portion at the distal end does not tend to enter the larynx and therefore does not tend to get stuck onto the larynx, thus lowering the risk of undesired insertion of the distal end of the mask into the larynx. In other words, the distally curved portion helps to scoop behind the larynx to make the distal end of the mask easily slide behind the larynx.

The upwardly extending portion may include one or more openings formed therein to facilitate fluid flow from the oesophagus to the proximal side of the mask during use of the mask. The upwardly extending portion may be defined by an upwardly extending wall and the opening may be in that wall.

In some embodiments of the present invention, the distal end of the mask may have a large radius of curvature. This will result in the distal end of the mask having a relatively "blunt" appearance. This is also believed to assist in facilitating insertion of the mask into the airway of a patient as the mask is less likely to snag on the structures at the back of the throat of the patient or on the inlet to the larynx.

In some embodiments, the peripheral portion of the mask may include an inflatable cuff, with the soft, flexible membrane extending from the inflatable cuff.

The distal end of the opening of the mask through which ventilation gases are supplied to the patient may be provided with a sloped region or a ramp. This sloped region or ramp allows the larynx to more easily slide over it during insertion of the mask, thereby ensuring that the larynx is properly positioned. Further, the larynx tends to become seated in the opening, thereby preventing the mask from being inserted too far into the patient and assisting in correctly positioning the mask in the patient.

The mask may be provided with one or more openings at or near its distal end, the one or more openings allowing fluid communication between the oesophagus and the throat region when the mask is inserted into a patient.

The mask may be provided with one or more longitudinally extending passageways or cavities that, in use, are in fluid communication with the oesophagus. These one or more longitudinally extending passageways or cavities may be in fluid communication with one or more openings formed in the distal tip of the mask. The one or more longitudinally extending passageways or cavities are physically separated from the airway tube and chamber of the mask so that any fluid that may move into the longitudinally extending passageways or cavities cannot be aspirated into the lungs of the patient.

In some embodiments, the mask of the present invention includes a central portion defining a chamber that is in fluid communication with the airway tube and, in use, in fluid communication with the larynx of a patient. A peripheral portion of the mask may be formed by the lower extremities of the chamber extending downwardly and then inwardly to thereby define a peripheral portion that, in use, forms a seal with the larynx. The peripheral portion may include the soft flexible membrane. The proximal portion of the chamber may form the proximal portion that is adapted to collapse. The dorsal surface of the mask may be positioned above the chamber. The dorsal surface may include a portion that extends laterally past an upper part of the chamber. As the lower peripheral surface (or ventral peripheral surface) of the mask is formed by a downwardly extending portion and an inwardly extending portion, the lateral part of the dorsal surface and the outer edges of the peripheral portion on the ventral side of the mask may define a passageway or an opening that enables fluid communication between the oesophagus and the proximal part of the mask when the mask is in use.

In another embodiment, the mask may include a longitudinally extending wall spaced from the part of the dorsal surface that extends laterally past an upper part of the chamber. This longitudinally extending wall may define a flow passage with the part of the dorsal surface that extends laterally past an upper part of the chamber and a further flow passage with an upper part of the chamber.

In most embodiments of the present invention, the flow passages have at least one open side. It is believed that providing an open side to the flow passages allows the mask to more readily deform during insertion of the mask to thereby assist in the insertion of the mask.

In some embodiments, the mask further includes a cricoid contacting portion that extends towards the cricoid cartilage and abuts with the cricoid cartilage when the mask is properly inserted, the cricoid contacting portion being adapted to form a seal in the vicinity of the cricoid cartilage.

In some embodiments, the mask includes a distal portion that extends past the cricoid cartilage when the mask is properly inserted, The cricoid contacting portion of the mask that extends towards the cricoid cartilage may comprise a projection extending away from the inner or ventral side of the dorsal wall of the mask. This extension may extend in a ventral direction within the airway cavity or airway chamber within the mask portion. The cricoid contacting portion may be made from a resilient material so that when the portion abuts with the cricoid cartilage, it pushes the cricoid cartilage away from the posterior pharyngeal wall. This may create an actual space between the cricoid cartilage and the posterior pharyngeal wall. In some embodiments, the cricoid contacting portion of the mask may exert pressure against the posterior and the posterolateral sides of the cricoid cartilage. This acts to open the crico-pharynx and the upper end of the oesophagus to allow a free flow of fluid from the oesophagus to the rest of the pharynx and this, in turn, may allow any fluid regurgitated from the stomach to be cleared by suction.

Additionally, the cricoid contacting portion of the mask that abuts with the cricoid cartilage forms an improved seal between the cricoid contacting portion of the mask and the cricoid cartilage, thereby improving the seal around the larynx that can be attained using the mask. Further, the cricoid contacting portion also ensures that the upper oesophagus is placed in and remains in good fluid communication with the sump area and the passageways in the mask. The sump area is formed by the passageways in the side of the mask portion, the opening in the distal end of the mask and by any transversely extending openings in the mask that allow fluid communication between the passageways.

The cricoid contacting portion that extends towards the cricoid cartilage may be shaped such that the posterior portion of the cricoid cartilage snugly fits into the cricoid contacting portion. The cricoid contacting portion also forms an improved seal in the vicinity of the cricoid cartilage.

The cricoid contacting portion may have a resilient and conformable surface that, in use, abuts with the cricoid cartilage. This allows the surface that abuts with the cricoid cartilage to form a very good seal in the vicinity of the cricoid cartilage.

The cricoid contacting portion may be in the form of a sling into which the cricoid cartilage snugly fits.

The region of the mask portion positioned dorsally of the cricoid contacting portion may act like a bridge. The bridge may have one or more openings therein (which may be transverse openings) which provide fluid communication laterally between the passageway on one side of the mask portion and the passageway on the other side of the mask portion. This opening or openings allows any regurgitated fluid to travel between the passageways on either side of the mask and also form a large sump area for collecting regurgitated fluid. Further, by applying suction to only one of the passageways, fluid can be removed via that passageway. Venting air can travel up the other passageway so that the formation of a negative pressure zone in the sump area is avoided. The openings in the bridge allow proper fluid communication between the passageway that has suction applied to it and the passageway that allows venting air to flow along it, so that venting air can readily flow up the passageway, through the openings (and thus flow laterally across the mask) and then down the passageway that has suction applied to it.

The mask portion may also define a sump area. The sump area may be defined by the passageways, and the transverse openings through the mask. The opening or openings at the distal end of the mask also form part of the sump region or sump area.

The cricoid contacting portion technically forms a new concept of posterior cricoid pressure which enables the fluid from the oesophagus to flow easily, enabling that fluid to be quickly cleared from the sump area by applying high suction to one of the passageways in the mask, or at least to allow regurgitated fluid to easily flow out of the upper oesophagus, which assists in preventing a build-up of fluid under pressure in the upper oesophagus, which can be potentially dangerous for causing aspiration of fluid into the lungs of the patient.

The mask may have a chamber having an inner wall, the chamber facing towards the larynx during use of the mask. The peripheral portion of the mask suitably extends around the chamber. The peripheral portion of the mask is suitably formed as an extension of the ventral part of the chamber. The chamber is in fluid communication with the airway tube such that gases can be delivered from the airway tube into the chamber and thereafter into the larynx and trachea of the patient. The cricoid contacting portion may extend away from a dorsal inner wall of the chamber. Alternatively, the cricoid contacting portion may comprise a projection or elevation that is ventrally located relative to the dorsal inner wall of the chamber.

The cricoid contacting portion may be located towards the distal end of the mask.

The distal end of the mask may include a region that extends towards the dorsal side of the mask. This region may comprise a ramp or sloped region that extends towards the dorsal side of the mask. This region may comprise a distal extension of the cricoid contacting portion.

In some embodiments, the cricoid contacting portion applies pressure to the cricoid cartilage using a spring action effect from within the mask. This helps to achieve a complete seal around the larynx which, in turn, allows a higher IPPV pressure and prevent aspiration of fluid regurgitated from the stomach. This isolates the air passage or trachea from the oesophagus but allows the oesophagus to be drained in the event that fluid from the stomach travels up the oesophagus.

In some embodiments, the device may include ventral curvature at the proximal portion of the mask, or near where the mask and airway tube joint or merge. It is believed that this assists in inserting the mask into the patient. In some embodiments, the mask may further include curvature in the opposite direction in a region of the airway tube that is proximal to the ventral curvature. This helps to push the tip of the mask dorsally during insertion, which assists in forwarding or minimising the likelihood of snagging of the mask on the larynx during insertion. Providing a dorsally extending ramp at or near the distal end of the mask also assists in this regard.

In some embodiments, a soft flexible membrane may be shaped such that it extends into and fills the piriform recess when the mask is supplied with ventilation gas. The piriform recess is a structure near the entrance to the larynx. This structure provides a soft area on either side of the larynx that does not have underlying bone or cartilage supporting it. Therefore, the piriform recess is a site for potential leaks when the mask is inserted into the patient in currently available laryngeal masks. By providing the soft flexible membrane, the ventilation gases can cause the soft flexible membrane to bulge into the piriform recess, entrapping the ventilation gases and to therefore provide an enhanced seal in the region of the piriform recess.

In some embodiments, the device may be used to facilitate intubation of a patient. In such embodiments, the dorsal wall of the mask portion may include a ventral extension which acts as a ramp or a guide to guide an end of an endotracheal tube being inserted through the mask through the opening of the mask and into the trachea of the patient. In one embodiment, the ventral extension may form an additional extension extending from the cricoid contacting portion of the mask. Alternatively, the ventral extension may comprise a separate structure just proximal to the cricoid contacting portion extending across the under surface of the dorsal wall within the airway chamber.

In other embodiments, the device may include a barrier extending upwardly into the chamber of the mask portion, the barrier forming a guide to guide an end of an endotracheal tube being inserted through the mask through the opening and into the trachea of a patient.

In one embodiment, the barrier comprises a flap. The flap may have a free end or a free edge. The flap may have a tapering width as it extends in an upwardly direction. In another embodiment, the barrier comprises a wall portion extending upwardly from a distal end of the opening in the mask towards the dorsal side of the mask.

In one embodiment, the flap extends upwardly from around a distal portion of the opening.

In one embodiment, the dorsal wall of the mask portion is shaped to receive the flap. For example, the dorsal wall may include a recess formed in the dorsal wall of the chamber, said recess receiving the flap. Alternatively, where the dorsal wall includes a ventral extension that is separate to the cricoid contacting portion, the ventral extension may extend ventrally from the inner dorsal wall from a position proximal to the cricoid contacting portion, the ventral extension including a distal portion that extends dorsally, and the cricoid contacting portion extending ventrally from the distal portion of the ventral extension. In this embodiment, the distal end of the ventral extension defines a recess positioned distally of the ventral extension, which recess can receive the barrier or flap.

In one embodiment, the barrier or flap moves into the recess when the device is inserted into a patient. In this regard, inserting the device into the patient may deform the peripheral portion of the device (by virtue of the interaction between the peripheral portion of the device and the tissues of the patient), said deforming causing the flap to move so that it extends into the recess. In some embodiments, the flap may lie against a wall of the recess, or the flap may lie against the cricoid contacting portion. In this embodiment, the flap presents a surface to an endotracheal tube, and therefore causes the end of the endotracheal tube to move along the flap and out through the opening in the device as the endotracheal tube is inserted.

The recess may have a proximal end wall that extends below an upper end of the flap when the flap is extending into or lying in the recess. In this manner, a free end of the flap cannot come into contact with the end of the endotracheal tube as the endotracheal tube will contact the proximal end wall of the recess and slide below the free end of the flap as the endotracheal tube is inserted. Suitably, the proximal end of the dorsal wall includes a portion that extends towards the ventral side of the mask, with the dorsal wall extending upwardly at the proximal end of the recess, the recess including a downwardly extending distal portion.

The mask of these embodiments is particularly suitable for intubating a patient or for inserting other equipment into the trachea of the patient.

In some embodiments, the soft flexible portion has a thickness of between 0.1 mm to 1 mm, more suitable from 0.1 mm to 0.6 mm. The soft flexible portion will generally have a thinner wall thickness than other parts of the mask.

In some embodiments in which the middle part of the mask is provided with a region of relatively higher strength or stiffness to facilitate pushing of the mask during insertion, the region of relatively higher strength or stiffness comprises a region having increased wall thickness and the region of increased wall thickness has a wall thickness of at least 1 mm.

The mask may be made from any suitable polymeric material, such as elastic polymers, medical grade polymers or food grade polymers, including silicone polymers, PVC, nitriles, urethanes, etc. The person skilled in the art will readily understand that a number of materials are suitable for use in manufacturing the device of the present invention.

The mask that the present invention is suitably made from medical grade silicone polymer having a Shore A hardness of from 20 to 50.

BRIEF DESCRIPTION OF DRAWINGS

Various embodiments of the invention will be described with reference to the following drawings, in which:

In FIG. 18, only the portion of the mask located above section line A-A is shown;

DESCRIPTION OF EMBODIMENTS

It will be appreciated that the drawings have been provided for the purposes of illustrating preferred embodiments of the present invention. Therefore, it will be understood that the invention should not be considered to be limited solely to the features as shown in the attached drawings.

The airway device 10 shown in the attached drawings has a stem 12 and a mask 14. The airway device 10 shown the attached drawings is suitably moulded from a single material and, in this embodiment, the airway device 10 is made as a unitary device. The airway device 10 shown in the attached figures is made from medical grade silicone polymer. However, it will be appreciated that, in other embodiments, the stem 12 may be manufactured separately to the mask 14, with a stem 12 and the mask 14 subsequently being joined together.

Figure 6:
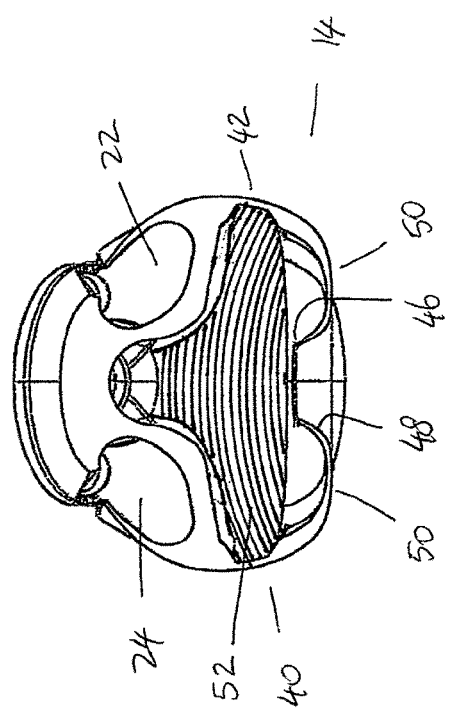
FIG. 6 shows a cross-sectional front view of the airway device shown in FIG. 2

The stem 12 includes an airway tube 16 and two fluid tubes 18, 20. The fluid tubes 18, 20 extend into fluid passageways 22, 24 (best shown in FIG. 6) that extended longitudinally along the mask 14. The fluid passageways 22, 24 have distal openings at the distal tip of the mask 14. In use, the fluid passageways 22, 24 allow any fluid material regurgitated from the stomach to pass along the fluid passageways and to be removed via the fluid tubes 18, 20. The distal tip of the mask 14 is provided with an extension 26. In use, extension 26 projects into the oesophagus. Any regurgitated fluid passes through extension 26 and into fluid passageways 22, 24. These features of the airway device are more fully described in our international patent application number PCT/AU2008/001259, the entire contents of which are incorporated here in the cross-reference. Accordingly, these features need not be described further.

The airway device 10 is also provided with a pull tab 28 that is connected at its distal end to a ventral part of the mask 14. The pull tab 28 is used to assist in inserting the mask into the patient. Further detail in this regard is provided in our international patent application number PCT/AU2010/000341, the entire contents of which are herein incorporated by cross reference.

The mask 14 (which may also be considered to be the mask portion of the airway device 10) has a proximal end generally shown at reference numeral 30 and a distal end generally shown at reference numeral 32. The mask 14 includes an airway chamber 34 (see FIG. 5) that is in fluid communication with airway tube 16. The chamber 34 includes an outlet 36. In use, gas is supplied through airway tube 16. The gas passes through the airway chamber 34 and exits the outlet 36. After exiting outlet 36, the gas enters the lungs of the patient.

Figure 5:
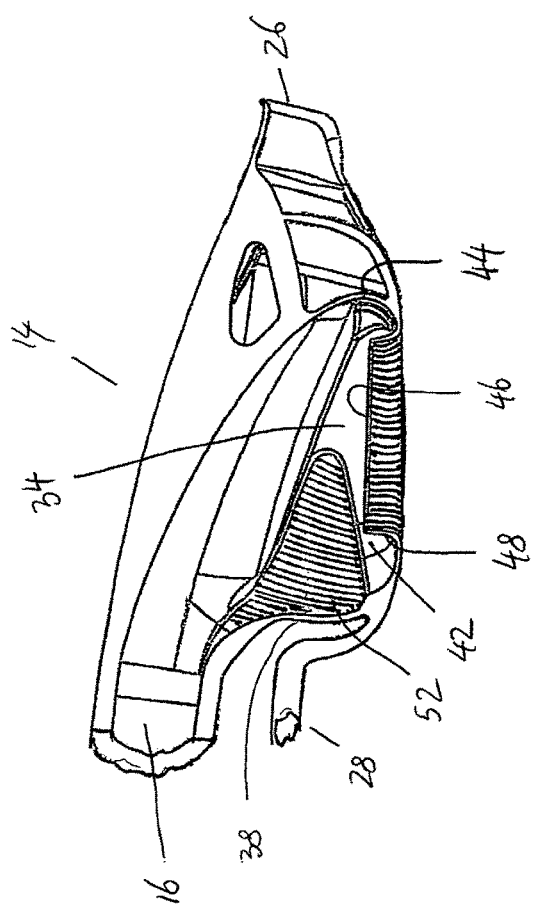
FIG. 5 shows a cross-sectional side view of the airway device shown in FIG. 2.

The airway chamber 34 has a proximal wall 38 and opposed side walls 40, 42. As shown in FIG. 5, the distal end of the airway chamber 34 merges downwardly and effectively defines a distal wall 44 of the airway chamber 34.

The outlet 36 of the airway chamber 34 has an inner periphery 46 (see FIGS. 5 and 6) that is defined by the upper end of an upwardly extending thin flexible wall portion 48. The thin flexible wall portion 48 then extends outwardly, as shown at reference numeral 50 in FIG. 6. The outwardly extending region 50 lies in abutment with the tissue surrounding the larynx when the airway device 10 is properly inserted in the laryngo pharynx of the patient. The outwardly extending region 50 then sweeps upwardly into the sidewalls 40, 42, the proximal wall 38 and the distal wall 44 of the airway chamber 34.

Figure 3:
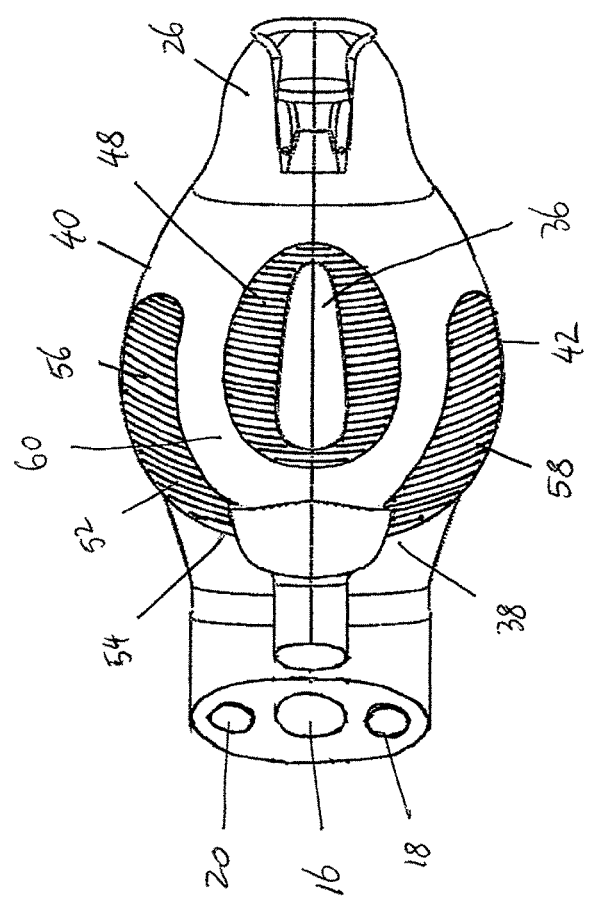
FIG. 3 shows a ventral-side view of the device shown in FIG. 2.
Figure 4:
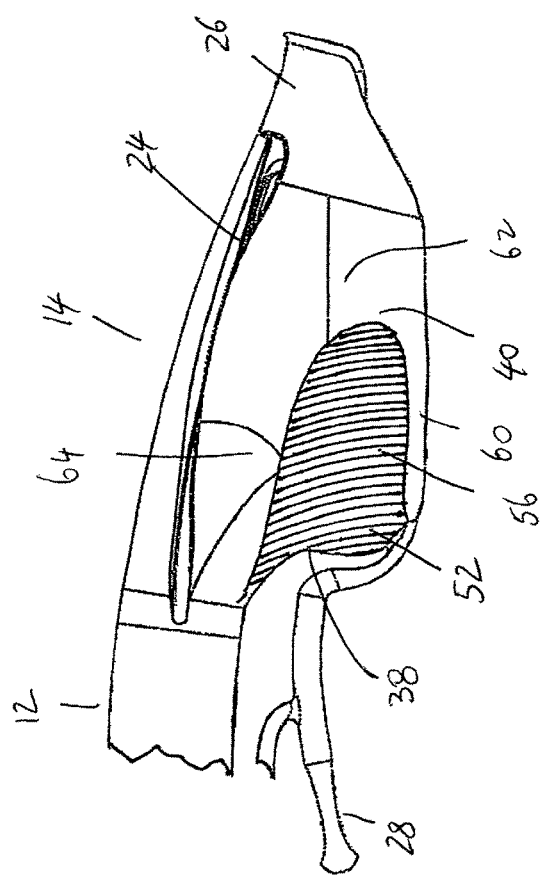
FIG. 4 shows a side view in cross section of the airway device shown in FIG. 2.

The thin flexible wall portion 48 is shown in shaded outline in FIG. 3. FIG. 3 appears to show that there is a sharp demarcation between the thin flexible wall portion 48 and the rest of the mask 14. However, in practice, the thickness of the wall may increase more gradually rather than having a step change in wall thickness.

Figure 1:
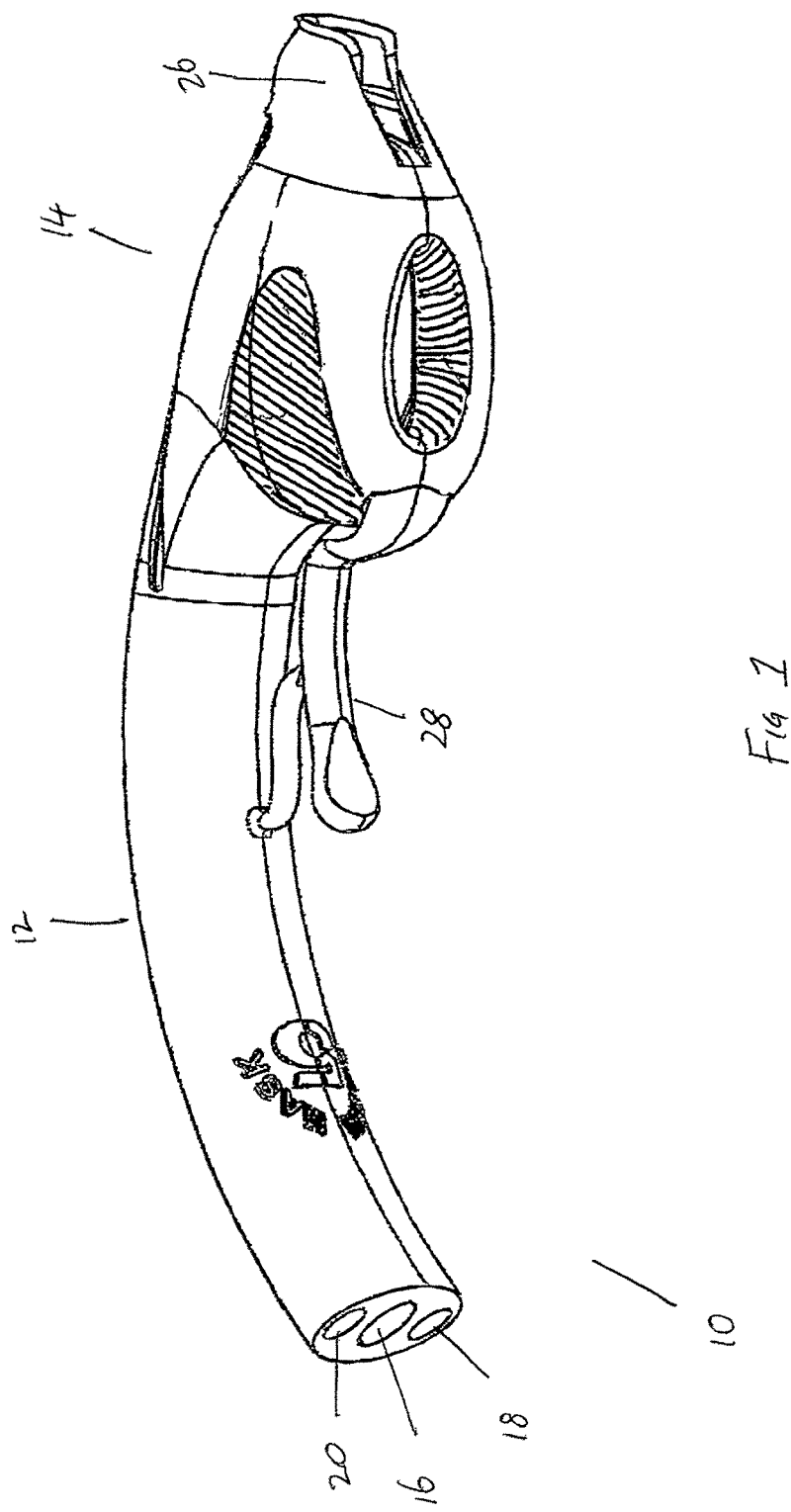
FIG. 1 shows a perspective view of an airway device in accordance with one embodiment of the present invention.
Figure 2:
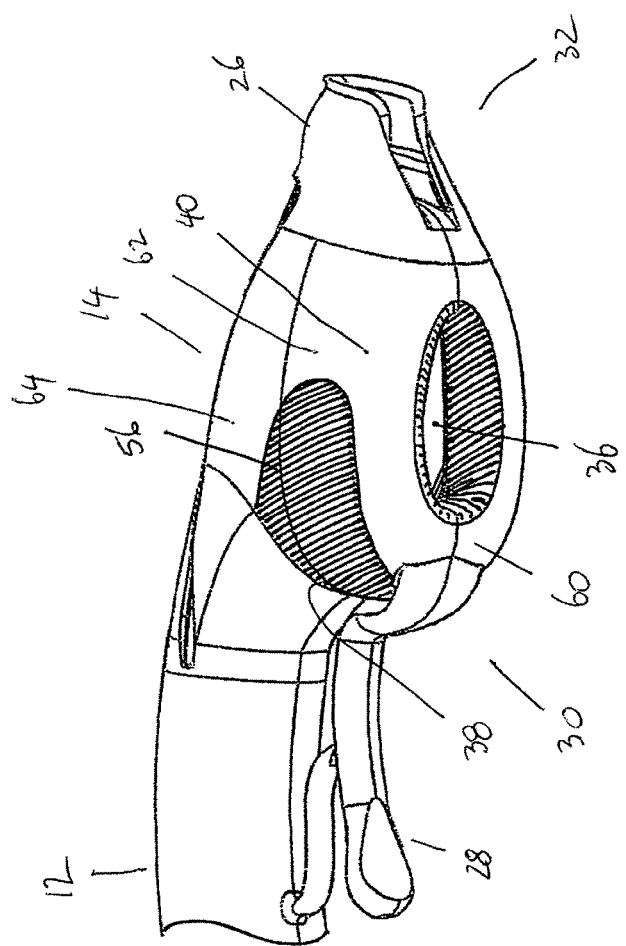
FIG. 2 shows a perspective view of the mask part and a small part of the airway tube of the airway device shown in FIG. 1.

The proximal end 30 of the mask includes a portion that is adapted to collapse or compress so that a proximal ventral part of the mask can move relatively towards a dorsal part of the mask, such as towards a proximal dorsal part of the mask, during insertion of the mask. This portion is shown in shaded outline at reference numeral 52 in FIGS. 1 to 6. As best shown in FIGS. 2 and 3, the portion 52 that is adapted to collapse or compress includes a portion 54 that extends across the proximal wall 38 of the airway chamber, a portion 56 that extends partly alongside wall 40 of airway chamber 34 and a portion 58 that extends partly alongside wall 42 of airway chamber 34. It will be appreciated that, in other embodiments (not shown), the portion that is adapted to collapse or compress may extend only in the proximal wall, or only in one or both side walls, or the side wall portions may be smaller than those shown in the attached drawings. The portion 52 that is adapted to collapse or compress is suitably formed by providing that region of the mask with a lower wall thickness such that less force is required to compress that portion of the mask. In other embodiments, the portion 52 may be made with a concertina type shape or a bellows type shape. In another embodiment, the portion 52 may be made from a material that has a lower strength than the material from which other parts of the mask are made. In another embodiment, the portion 52 may have alternating thin regions (or regions of lesser strength or stiffness) and thick regions (or regions of greater strength or stiffness). In the embodiment shown in the attached drawings, the portion 52 has a thinner wall thickness than other parts of the airway chamber (with the possible exception of the thin flexible wall portion 48).

In the airway device showing in the attached figures, the thin flexible wall portion 48 that surrounds the outlet 36 is itself surrounded by a region of relatively higher strength or stiffness, denoted generally at 60. As best shown in FIG. 3, the region 60 includes the material shown in white surrounding the thin flexible wall portion 48. The region 60 may comprise a region of thicker wall thickness, when compared to the thin flexible wall portion 48. For example, the thin flexible wall portion 48 may have a thickness of less than 0.5 mm, or even less than 0.3 mm, whilst the region 60 may have a wall thickness of 1 mm or greater.

In other embodiments, the region 60 may comprise a region that includes one or more reinforcing ribs. In other alternative embodiments, the region 60 may be made from a material having greater strength or stiffness in the material from which thin flexible wall portion 48 is made.

The region 60 is effective in maintaining the thin flexible wall portion 48 in its desired shape and orientation. In particular, if an anaesthetist pushes firmly on the stem of the airway device, distortion of the mask may be possible, which could cause of the thin flexible wall portion 48 to buckle. This could result in the airway passage into the patient becoming occluded or compromised. The region 60, which has higher strength or stiffness, is more resistant to changes of shape caused by forces applied to the airway device and thus the region 60 assists in maintaining the outlet 36 and the thin flexible wall portion 48 in the correct shape and orientation.

The region 60 also extends distally of the side wall portions 56, 58 of the proximal portion 52 that is adapted to collapse or compress. As can be seen from FIGS. 2 and 4, the region 60 extends distally of portion 56, as shown by reference numeral 62. The region 62 and then sweeps back dorsally and proximally, as shown at reference numeral 64 and effectively extends to at least partially surround the region 56. The shape of the regions denoted by reference numerals 60, 62 and 64 causes the region 60 to be effectively hinged or sprung to the dorsal part of the mask 14, with the hinge or spring effect largely acting close to the junction between thin flexible region 56 and region 62. As a result, when proximal portion 52 collapses during insertion of the airway device into the patient, the region 60 flexes at a position that is close to region 62. When the mask is positioned in the laryngo pharynx of the patient, the spring action of the regions 60, 62, 64 assists in expanding the mask to fully occupy the space in the laryngo pharynx. This, of course, expands the proximal portion 52 from the collapsed or compressed state that it assumed during insertion past the teeth to an expanded position, which is essentially as shown in FIG. 2. In the expanded position, the airway device is able to properly supply air or other gases to the patient's airway.

In another embodiment, the thin wall portion 48 may be replaced by a wall portion that is made from a material that is of lesser strength or greater flexibility than the material of the adjacent wall regions. For example, the wall portion 48 may be made from a gel material or a foam material. In this embodiment, the thickness of wall portion 48 may be the same as or greater than the thickness of the adjacent wall regions.

Figure 7:
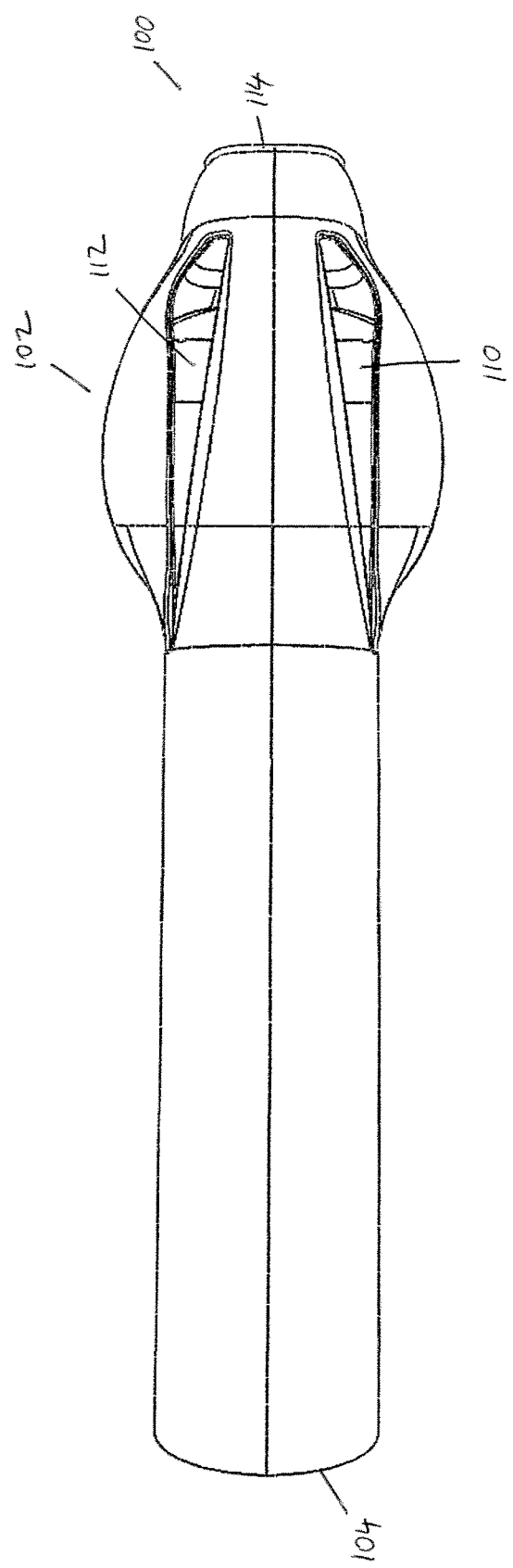
FIG. 7 shows a top view (from the dorsal side) of masks in accordance with another embodiment of the present invention. The three masks shown in FIG. 7 are identical, save for being of different sizes to fit into different sized patients.
Figure 8:
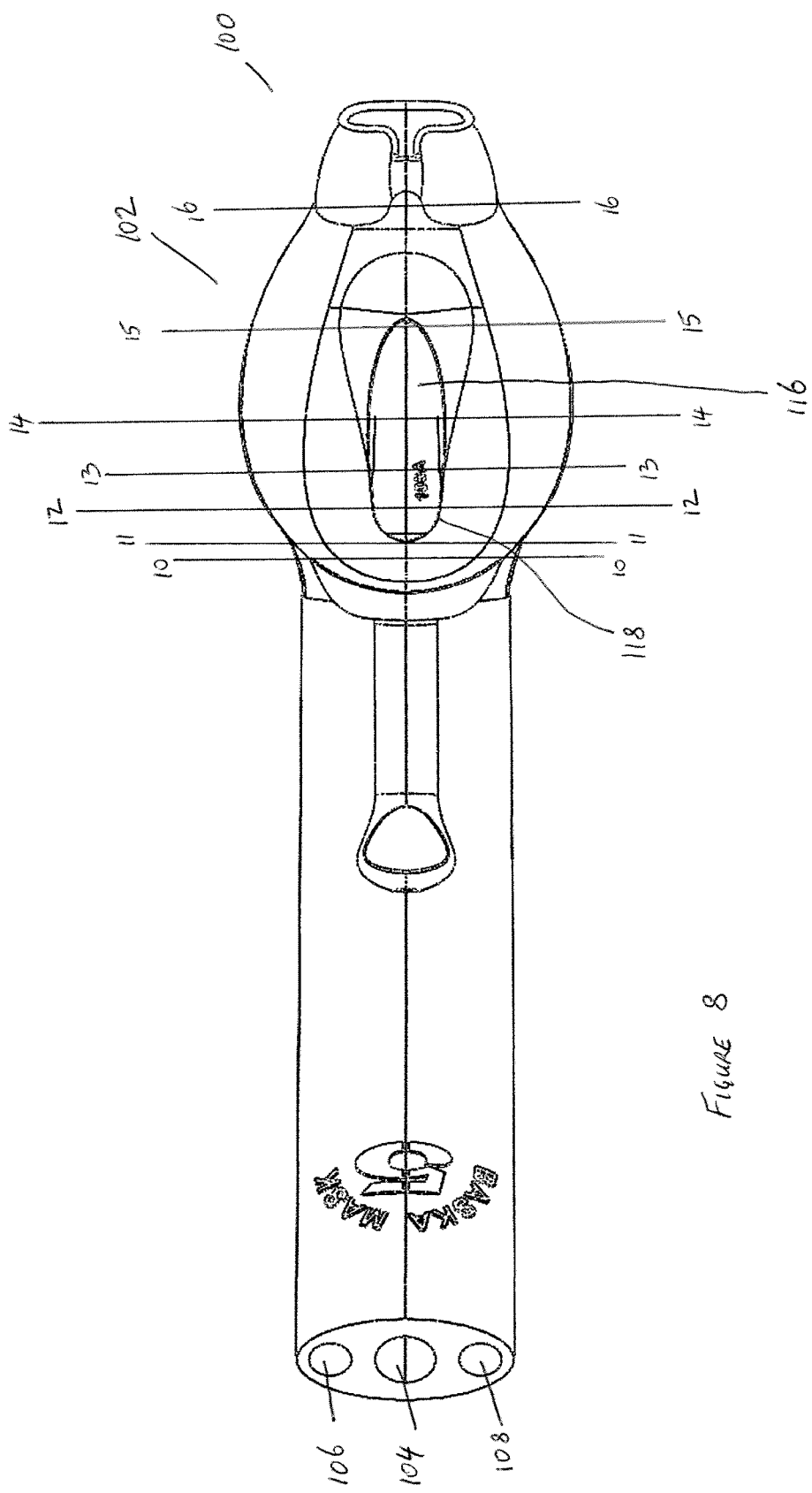
FIG. 8 shows a bottom view (from the ventral side) of the masks shown in FIG. 7.
Figure 9:
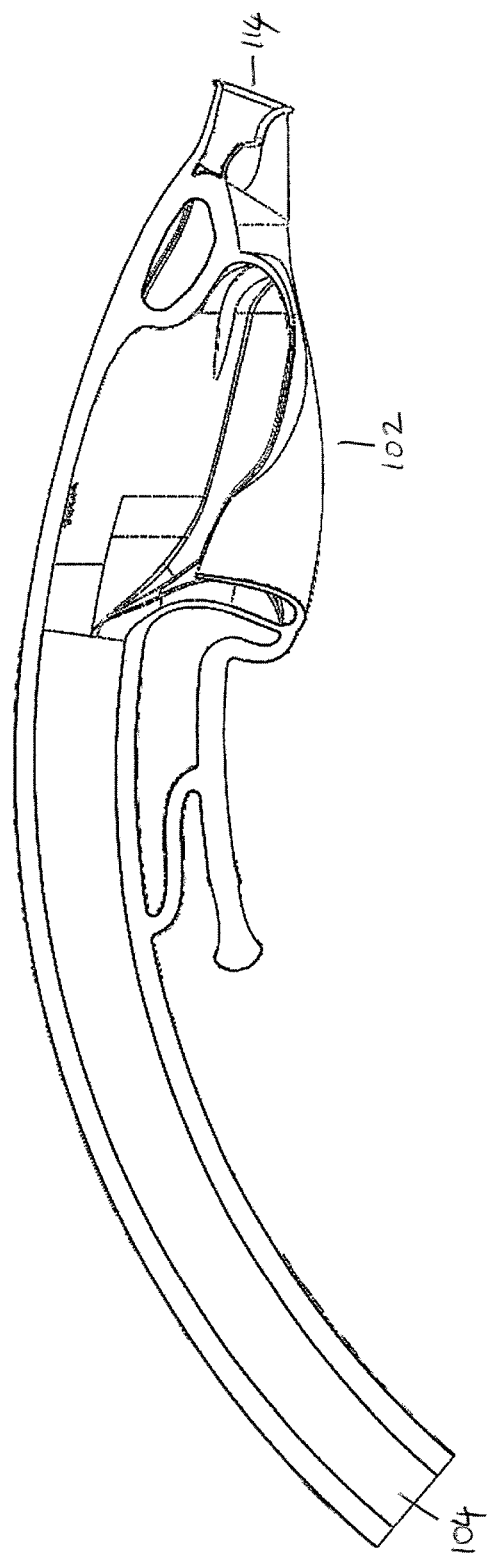
FIG. 9 shows a cross-sectional view of one of the masks shown in FIGS. 7 and 8, with the cross-section taken along a longitudinal centre line of the mask.

FIGS. 7 to 17 show various views of an airway device in accordance with another embodiment of the present invention. The airway device 100 shown in FIGS. 7 and 8 comprises a mask portion 102 and an airway tube 104 that is integrally formed with the mask portion 102. The airway device 100 may be manufactured by moulding. The airway device 100 may be made from a medical grade silicone material. As best shown in FIG. 8, two tubes or passageways 106, 108 extend generally parallel to the airway tube 104. Tubes or passageways 106, 108 extend into open passageways 110, 112 that extend along opposed sides of the mask portion 102. This is shown in FIG. 7. The open passageways 110, 112 have distal openings at the distal end of the mask portion 102. The mask portion 102 includes a protrusion 114 at its distal end. The distal openings of passageways 110, 112 open into the protrusion 114. In use, the protrusion 114 extends into the oesophagus of the patient and maintains the oesophagus in an open condition. In this way, if there is any vomitus expelled during a procedure, the vomitus can pass through protrusion 114 and along passageways 110, 112. Suction may be used to remove the vomitus via tubes or passageways 106, 108. In this regard, the construction of the airway device is similar to that described in Australian patent number 2004260552, the entire contents of which are incorporated herein by cross-reference.

The airway device 100 has an airway chamber 116 that is in fluid communication with the airway tube 104. The airway chamber has an opening 118 through which ventilation gases or anaesthetic gases can pass and be delivered to the lungs of a patient.

The airway device 100 shown in FIGS. 7 to 17 also has a number of other features that are common to the masks shown in FIGS. 1 to 6. For the sake of brevity of description, these features need not be described further.

Figure 10:
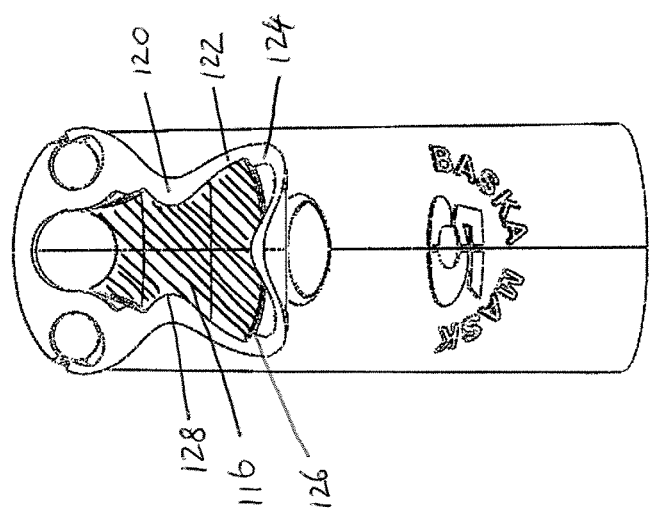
FIGS. 10 to 16 show various cross sectional interviews of a mask shown in FIGS. 7 and 8, with the various lines along which the cross sections were taking being shown in FIG. 8.
Figure 11:
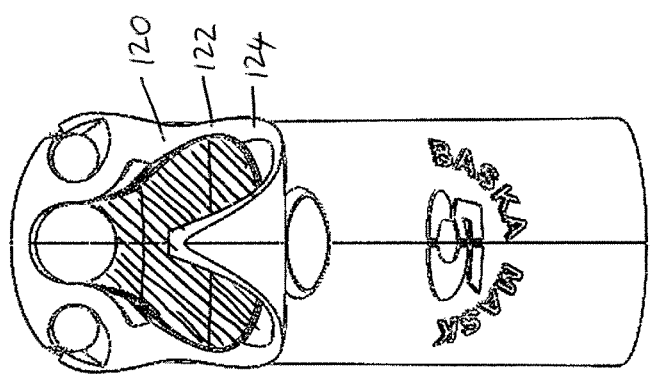

The mask portion 102 of the airway device 100 shown in FIGS. 7 to 17 includes a proximal portion that is adapted to collapse or compress during insertion of the mask into a patient. This proximal portion can be seen more clearly in the cross sectional end views shown in FIGS. 10 to 17. The cross-sectional end views shown in FIGS. 10 to 17 are taken along the cross-sectional lines of the corresponding numbers that are shown in FIG. 8. For example, the view shown in FIG. 10 is taken along the cross-sectional line numbered "10" in FIG. 8, the cross-sectional view in FIG. 11 is taken along the cross-sectional line numbered "11" in FIG. 8, and so forth.

Turning now to FIG. 10, it can be seen that the proximal wall portion of the mask portion 102 includes a first region 120 that curves inwardly and a second region 122 that extends ventrally from first region 120 and extends outwardly from first region 120. The effect of this is to result in second region 122 in the wall defining a recess in the proximal wall portion of the chamber 116.

The lower end of second region 122 merges into a third region 124 that moves inwardly relative to the second region 122. As can be seen from FIG. 10, the third region 124 has a region 126 that defines a projection or protrusion in the proximal wall portion of the mask.

Due to the geometry of the portions shown in FIG. 10, during insertion of the mask, the second region 122 flexes outwardly relative to first region 120 and the third region 124 (and regions located ventrally of region 124) flex upwardly relative to the second region 122. This shortens the distance between the dorsal and ventral sides of the proximal portion of the mask portion 102 during insertion, thereby facilitating insertion of the mask.

FIG. 11 is a cross sectional view taken along line 11 in FIG. 8. As can be seen from FIG. 11, the first region 120, the second region 122 and third region 124 are still discernible. However, the angle between the first and second regions and the angle between the second and third regions is less than that shown in FIG. 10. As a result, the amount of flex (which equates to the amount of compressing or collapsing of the mask occurring in this part of the mask) during insertion will be reduced.

Figure 12:
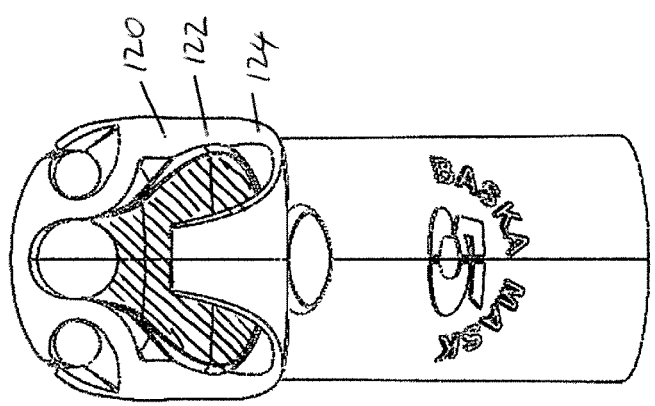

FIG. 12 is a cross-sectional view taken along the line 12 in FIG. 8. As can be seen from FIG. 12, the angle between the first region 120 and the second region 122 is even further reduced. Similarly, the angle between the second region 122 and the third region 124 is further reduced, As can be seen from FIGS. 10 to 12, the first region 120 has a curved inner wall 128 that defines a protrusion in the proximal wall of the chamber 116.

Figure 13:
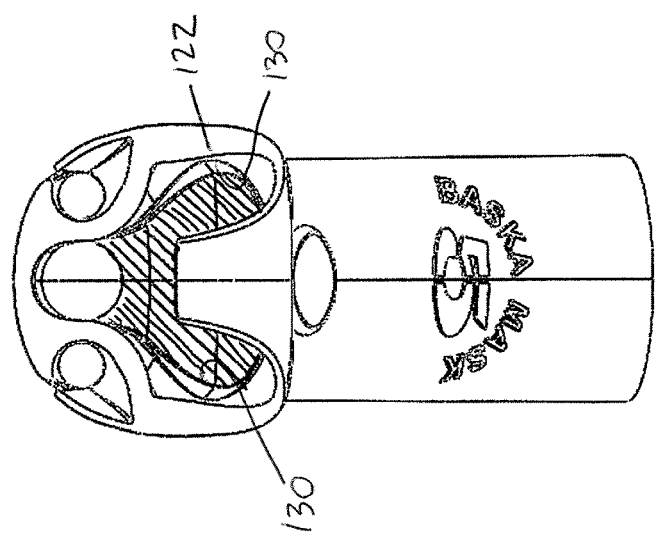

The cross-sectional view shown in FIG. 13 shows that the region of the proximal part of the mask that is adapted to collapse or compress is nearing its end. The vestigial remains of second region 122 can be seen in FIG. 13. FIG. 13 also clearly shows the region 130 that is adapted to collapse or compressed during insertion of the mask into a patient. The region 130 comprises a recess in the proximal wall of the mask. The region 130 also forms a region of thinner wall thickness in the proximal wall of the mask.

Figure 14:
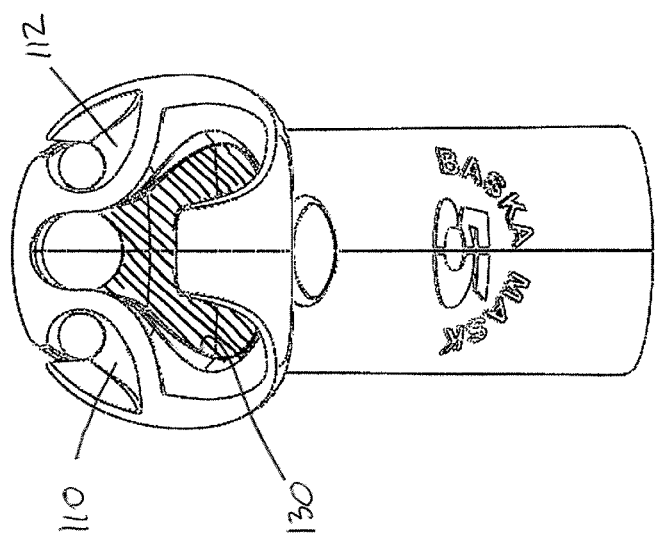

FIG. 14 is a cross-sectional view taken along line 14 of FIG. 8. The passageways 110, 112 can clearly be seen in FIG. 14. The region 130 in the proximal portion of the mask portion 102 can also be clearly seen in FIG. 14.

Figure 15:
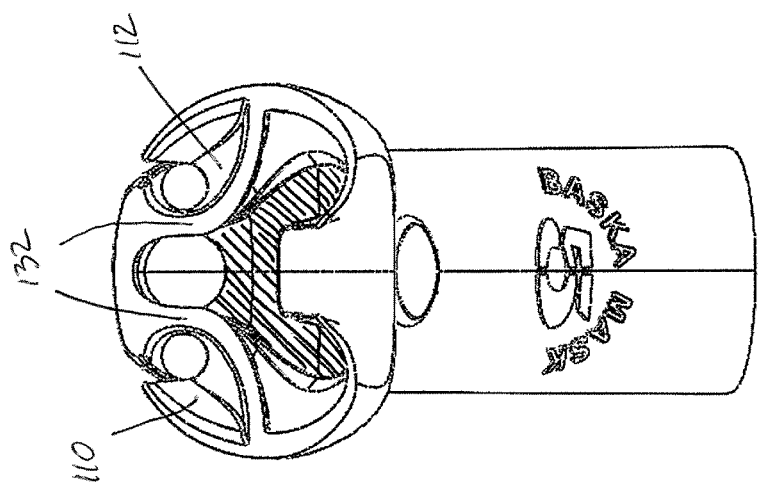
Figure 16:
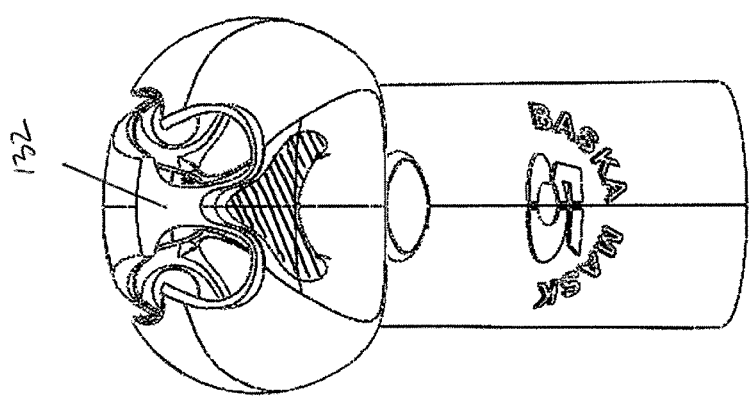
Figure 17:
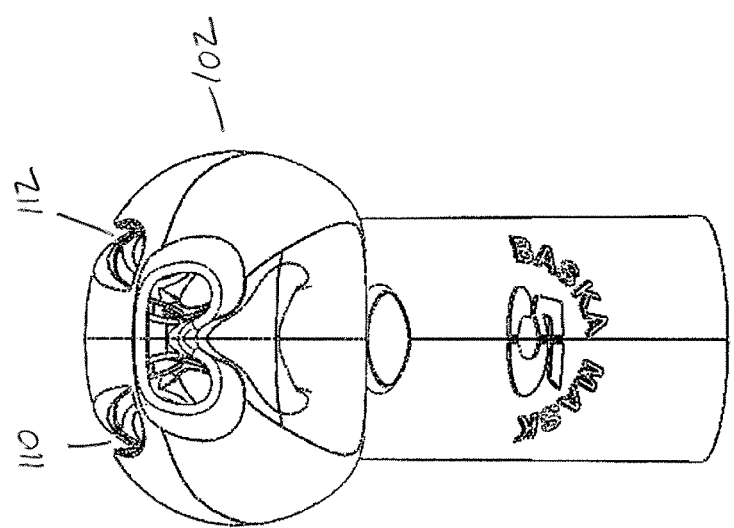
FIG. 17 is an end view (looking towards the distal end of the mask) of one of the masks shown in FIGS. 7 and 8.

FIG. 15 is a cross-sectional view taken along line 15 of FIG. 8. FIG. 15 clearly shows a thick wall portion 132 extending along the central part of the distal end of the mask. This provides good strength at this part of the mask, which assists in preventing the distal end of the mask from folding up during insertion. The region comprising thick wall portion 132 can also be seen as continuing along the mask in FIG. 16.

In use of the airway device shown in the attached figures, the mouth of the patient is opened and the mask inserted into the mouth. As the mask portion of the airway device moves past the teeth, the relatively narrow profile and lesser height of the distal part of the mask easily passes into the mouth and past the teeth. However, the proximal portion of the mask has a significantly higher profile. As the proximal portion of the mask is pushed in past the teeth, the proximal portion 52 collapses or compresses to lower the height of the proximal portion of the mask, thereby allowing the proximal portion of the mask to pass between the teeth. The region of higher strength or stiffness 60 assists in preventing the mask from folding back on itself as insertion continues. The anaesthetist continues to push on the stem of the airway device and the mask continues to move along the throat of the patient until the mask portion reaches the laryngo pharynx. In the fully inserted position, the hinging action or spring action of the regions 60, 62, 64 assist in expanding the collapsed proximal region 52 of the mask. Anaesthetic gases or ventilation gases are then supplied to the patient. As the pressure of the gas supply to the patient increases during the regular breathing cycle, the gases act to urge the thin flexible wall portion 48 into contact with the tissue surrounding the larynx. This assists in forming an effective seal to prevent leakage of gas from the airway chamber. Furthermore, as an effective seal is achieved between the mask portion of the airway device and the larynx of the patient, fluids (such as regurgitated fluids or vomitus) are prevented from entering the lungs whilst the airway device is in position. If any fluid is regurgitated from the stomach, it can pass through the fluid passageways 22, 24 and be removed by fluid tubes 18, 20. It is possible that one of the fluid tubes may be used for suction and the other fluid tube may be used to allow venting air to be provided.

Figure 18:
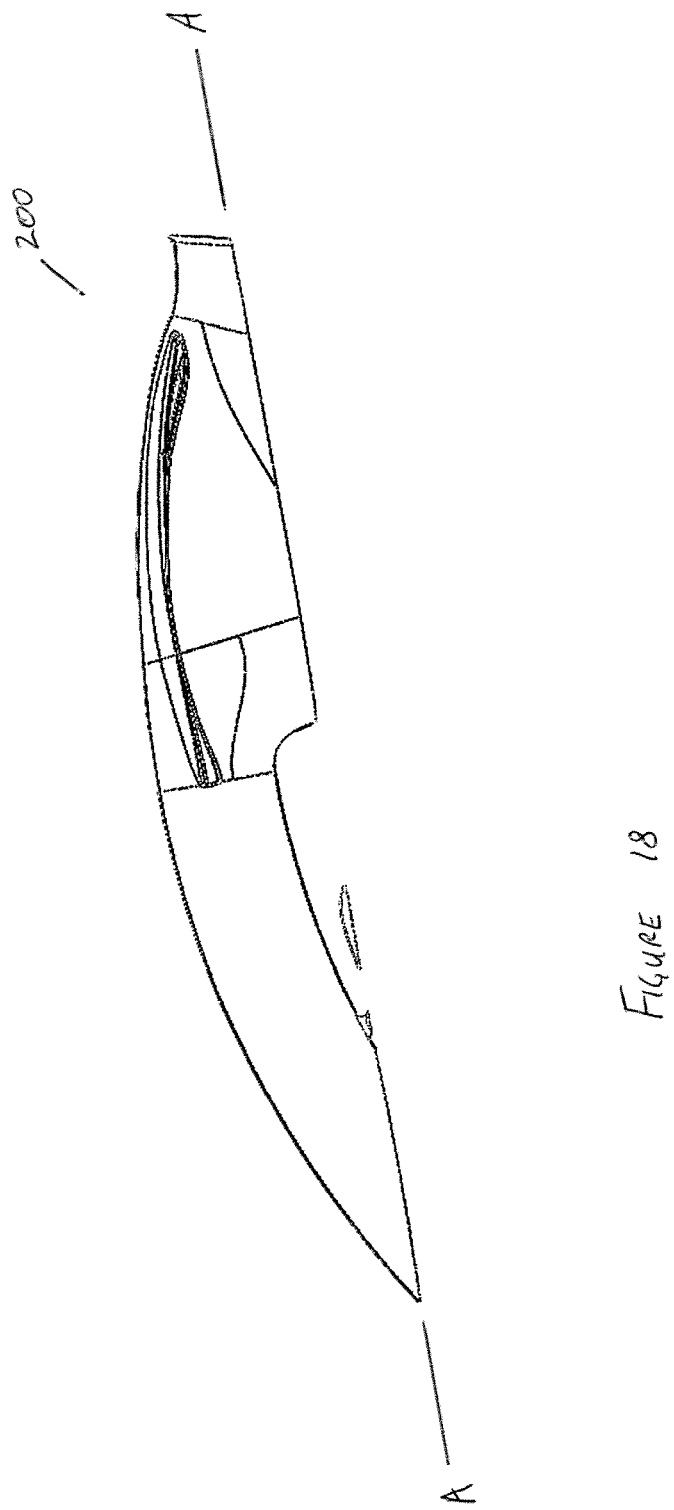
FIG. 18 is a side view of an airway device in accordance with another embodiment of the invention.
Figure 19:
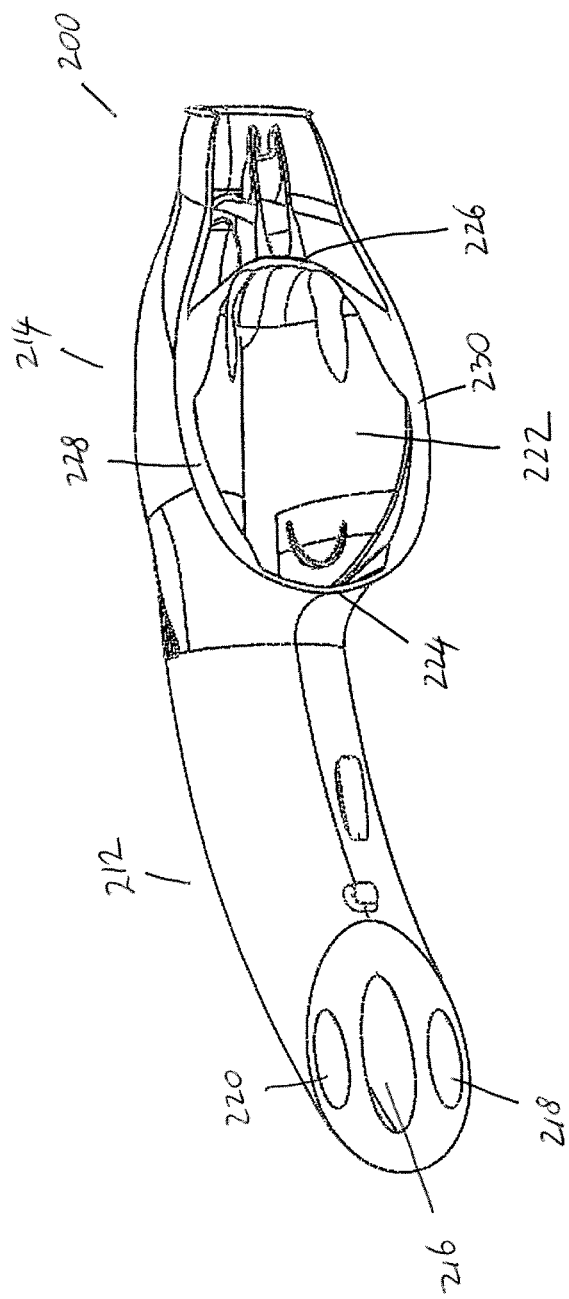
FIG. 19 shows a perspective view from underneath of the airway device shown in FIG. 18. The perspective view is a cross-sectional view taken along the section line A-A.
Figure 20:
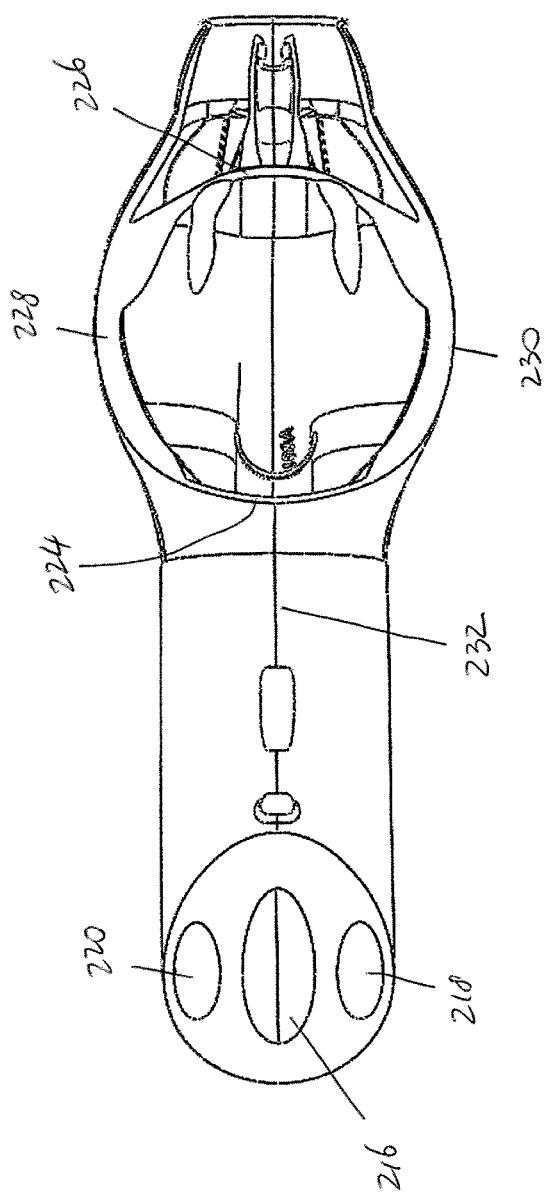
FIG. 20 shows an underneath cross-sectional view of the airway device shown in FIGS. 18 and 19.

FIGS. 18 to 20 show various views of an airway device in accordance with another embodiment of the present invention. The view of the airway device 200 shown in FIGS. 18 to 20 is a cross sectional view that is taken along a cross section denoted by section line A-A in FIG. 18. In FIG. 18, the region of the airway device 200 that appears below the section line A-A has been omitted. The region below section line A-A may be similar to that as shown in any of FIGS. 1 to 17, or similar to that as shown in our international patent application number PCT/AU2008/001259.

In FIGS. 19 and 20, the airway device 200 can be seen as comprising a stem 212 and a mask portion 214. The stem 212 includes airway tube 216 and fluid passageways 218, 220. FIG. 19 also shows the upper part of the airway chamber 222. Airway chamber 222 is in fluid communication with airway tube 216. The chamber 222 has an opening that, in use, overlies the laryngeal opening and allows ventilation gases or anaesthetic gases to be supplied to the lungs of the patient.

As can be seen from FIG. 19, the airway chamber 222 has a proximal wall 224, a distal wall 226 and side walls 228, 230. The proximal wall 224 and the distal wall 226 have a thickness that is less than the thickness of the side walls 228, 230. For example, in FIG. 20, the proximal wall portion 224A may have a thickness of 0.15 mm and the distal wall portion 226A may have a thickness of 0.2 mm. The side wall portions 228A, 230A may have a thickness of 3 mm. In this manner, the proximal wall 224 and the distal wall 226 defining the airway chamber 222 can collapse, deform or compress more readily than the side walls 228, 230. As a result, the midline of the mask portion of airway device 200 can readily adopt a low profile during insertion of the mask. This has been found to greatly facilitate insertion of the mask. The midline of the mask is more clearly shown in FIG. 18 at reference numeral 232.

Figure 21:
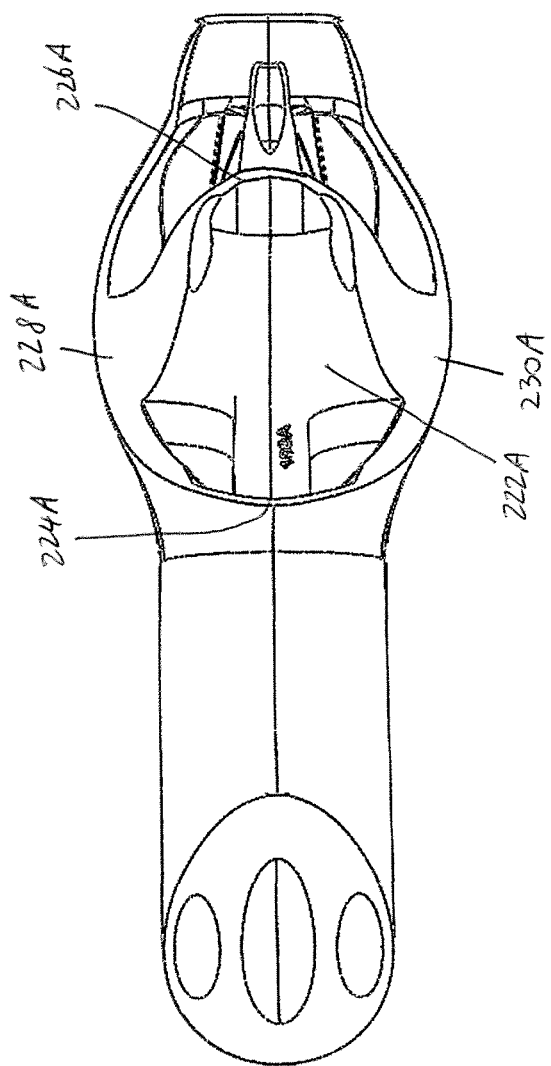
FIG. 21 shows an underneath cross-sectional view of an airway device in accordance with another embodiment of the present invention.

FIG. 21 shows a similar view to FIG. 20 but in an embodiment with a different shape to the airway chamber. In FIG. 21, the same reference numerals as used in FIG. 20 with the addition of "A" thereto are used to denote similar features. As can also be seen in FIG. 21, the proximal wall 224A and the distal wall 226A have a thickness that is significantly less than the thickness of the side walls 228A, 230A of the airway chamber 222A. For example, in FIG. 21, the proximal wall portion 224A may have a thickness of 0.35 mm and the distal wall portion 226A may have a thickness of 0.3 mm. The side wall portions 228A, 230A have a varying thickness that is significantly larger than the thickness of the proximal wall portion 224A and the distal wall portion 226A.

Figure 22:
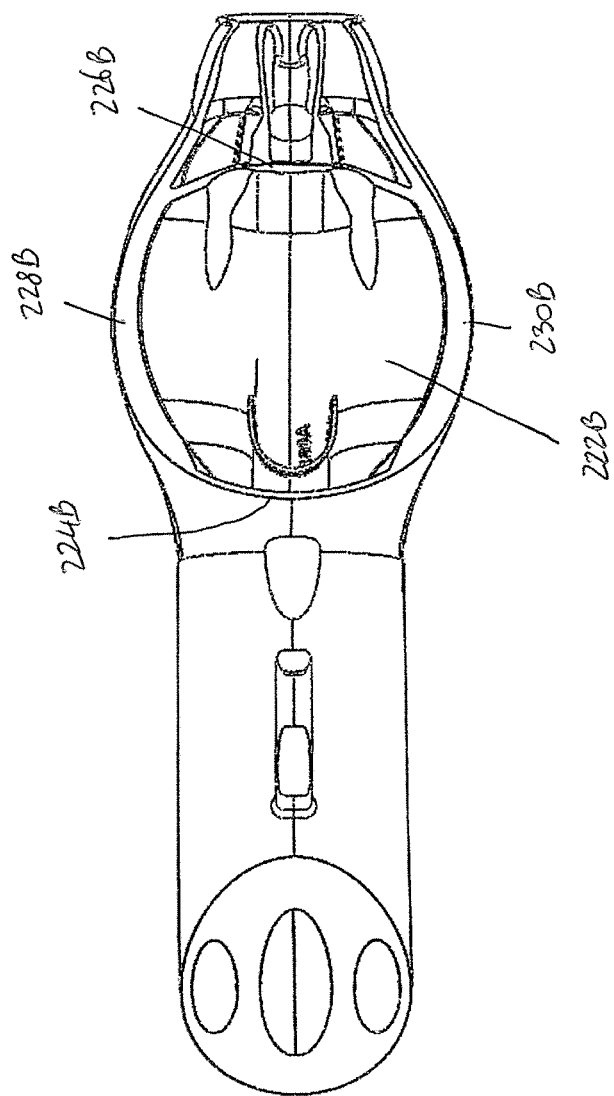
FIG. 22 shows an underneath cross-sectional view of an airway device in accordance with another embodiment of the present invention.

FIG. 22 shows a similar view to FIG. 20 but in an embodiment with a different shape to the airway chamber. In FIG. 22, the same reference numerals as used in FIG. 20 with the addition of "B" thereto are used to denote similar features. As can also be seen in FIG. 22, the proximal wall 224B and the distal wall 226B have a thickness that is significantly less than the thickness of the side walls 228B, 230B of the airway chamber 222B. For example, in FIG. 22, the proximal wall portion 224B may have a thickness of 0.1 mm and the distal wall portion 226B may have a thickness of 0.15 mm. The side wall portions 228A, 230A may have a thickness of 2.4 mm.

Figure 23:
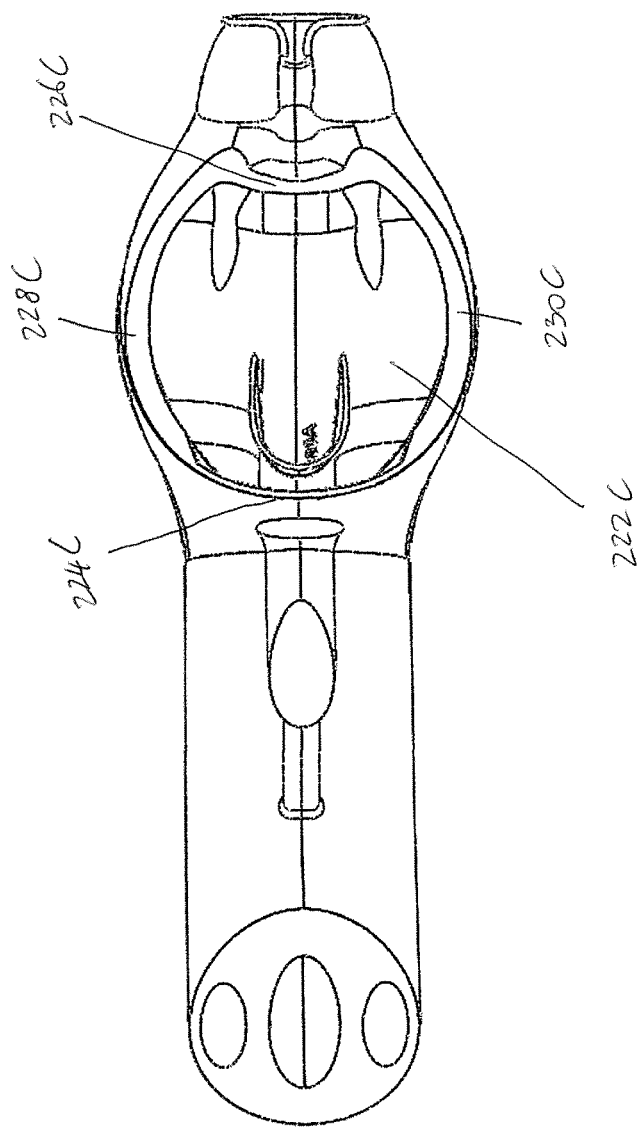
FIG. 23 shows an underneath cross-sectional view of an airway device in accordance with another embodiment of the present invention.

FIG. 23 shows a similar view to FIG. 20 but in an embodiment with a different shape to the airway chamber. In FIG. 23, the same reference numerals as used in FIG. 20 with the addition of "C" thereto are used to denote similar features. As can also be seen in FIG. 23, the proximal wall 224C and the distal wall 226C have a thickness that is less than the thickness of the side walls 228C, 230C of the airway chamber 222C. As can also be seen in FIG. 23, the distal wall 226C has a larger thickness than the proximal wall 224C, although the distal wall still has a thickness that is less than the thickness of the side walls. In this embodiment, the proximal wall 224C will collapse or compress more readily than the distal wall 226C. However, as the height of the mask is lower at the distal end than at the proximal end, easy insertion of the mask is still possible.

Figure 24:
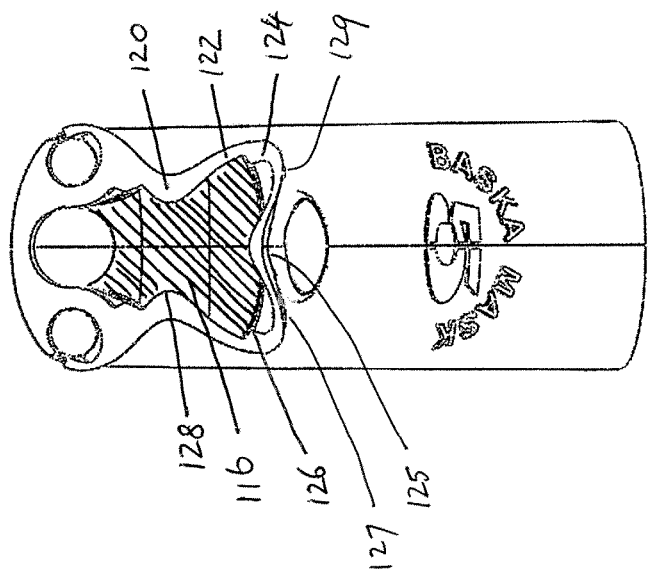
FIG. 24 shows an end cross-sectional view of an airway device in accordance with another embodiment of the present invention.

FIG. 24 shows a view of another embodiment of the airway device in accordance with the present invention. FIG. 24 is a view that is generally similar to FIG. 10 and, for convenience, like features will be denoted by like reference numerals. In the embodiment shown in FIG. 4, the ventral portion 125 of the proximal part of the mask is of lower profile than the immediately adjacent ventral portions 127, 129 of the mask. As can be seen from FIG. 24, the ventral portion 125 dips upwardly towards the dorsal part of the mask. In this arrangement, insertion of the mask is facilitated. The wall thickness at the proximal part of the mask may be similar to the adjacent wall thickness in this embodiment. The ventral portion 125 may be made from the same material as the immediately adjacent ventral portions 127, 129.

The airway device of embodiment of the present invention has a mask portion in which a rear or proximal portion of the wall surrounding the airway cavity/airway chamber is structurally different to the wall regions located adjacent thereto. In some embodiments, the distal or front portion of the wall surrounding the airway cavity is also structurally different to the wall regions located adjacent thereto. The proximal portion and the distal portion of the wall surrounding the airway cavity/airway chamber may be made with a thin wall thickness, or they may be made to be more flexible than the adjacent wall regions. In some embodiments, the portions of the wall surrounding the airway cavity/airway chamber that are located on and adjacent the midline of the mask are structurally different to the adjacent portions of the airway cavity/airway chamber.

As the mask has walls defining the airway chamber that allow for preferential deformation, compression or collapse around the midline of the mask, the midline portions of the mask can collapse or be compressed during insertion to facilitate insertion. The side wall portions of the airway cavity/airway chamber support and hold the proximal and distal portions wants the mask has been inserted. Further, in embodiments where a thin membrane is located adjacent to the tissue structures surrounding the laryngeal opening during use, which membrane is shaped to partly capture gases supplied to the patient to cause the membrane to expand, the gases supplied to the patient will also assist in maintaining the shape of the airway chamber once the airway device has been fully inserted into the patient.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The invention claimed is:

1. A device for maintaining an airway in a patient, the device comprising a mask having a portion that forms a seal with the larynx when the mask is positioned in the laryngo pharynx to thereby prevent ingress of extraneous fluids into the larynx, and an airway tube connected to or formed with the mask for passing gas to the larynx when the mask is properly inserted into the laryngo pharynx, the mask includes a chamber having an opening in fluid communication with the airway tube, the chamber including an outlet through which pressurised gases are supplied to the patient, the chamber including a wall having a wall portion extending from a ventral side of the mask towards a dorsal side of the mask, the wall of the chamber includes a proximal wall portion, opposed side wall portions and a distal portion, the mask includes a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall, the chamber including a region of relatively higher strength or stiffness extending at least partly around a soft, flexible portion surrounding the outlet, wherein the mask includes a proximal portion adapted to collapse or compress so that a proximal ventral part of the mask can move relatively towards a dorsal part of the device during insertion of the mask, the region of relatively higher strength or stiffness being at least partly located in a region between the soft, flexible portion surrounding the outlet of the mask and the proximal portion that is adapted to collapse or compress.

2. A device for maintaining an airway in a patient as claimed in claim 1 wherein the mask includes a proximal portion that is adapted to collapse or compress and a distal portion that is adapted to collapse or compress.

3. A device for maintaining an airway in a patient as claimed in claim 2 wherein the proximal portion comprises a region having a lesser wall thickness than a wall thickness of adjacent regions and the distal portion comprises a region having a lesser wall thickness than a wall thickness of adjacent regions.

4. A device for maintaining an airway in a patient as claimed in claim 2 wherein the proximal region may comprise a region of a wall of a chamber and the distal region comprises a region of a wall of the chamber.

5. A device for maintaining an airway in a patient as claimed in claim 2 wherein the proximal portion has a different wall thickness to the distal wall portion.

6. A device for maintaining an airway in a patient as claimed in claim 2 wherein the proximal portion that is adapted to collapse or compress comprises a proximal region of the mask that is located near a mid-line of the mask, or extends to both sides of a midline of the mask.

7. A device for maintaining an airway in a patient as claimed in claim 2 wherein the distal portion that is adapted to collapse or compress comprises a distal region of the mask that is located near a mid-line of the mask, or extends to both sides of a midline of the mask.

8. A device for maintaining an airway in a patient as claimed in claim 7 wherein the mask includes a chamber having an outlet through which gases are supplied to the patient, the chamber including a region of relatively higher strength or stiffness extending at least partly around a soft, flexible portion surrounding the outlet, the region of relatively higher strength or stiffness extending at least partly around the soft flexible portion surrounding the outlet of the mask comprises a region of relatively high strength or stiffness surrounding the soft flexible portion, the region of relatively higher strength or stiffness being at least partly located in a region between the soft, flexible portion surrounding the outlet of the mask and the proximal portion that is adapted to collapse or compress.

9. A device as claimed in claim 8 wherein the ventral portion of the mask dips towards the dorsal side of the mask in the proximal region thereof.

10. A device for maintaining an airway in a patient as claimed in claim 1 wherein a middle part of the mask is provided with a region of relatively higher strength or stiffness to facilitate pushing of the mask during insertion.

11. A device for maintaining an airway in a patient as claimed in claim 1 wherein the region of relatively higher strength or stiffness comprises a region located in a middle part of opposed side walls of the mask.

12. A device for maintaining an airway in a patient as claimed in claim 11 wherein the region of relatively higher strength or stiffness comprises a region of larger wall thickness.

13. A device for maintaining an airway in a patient as claimed in claim 1 wherein the mask is made from medical grade silicone polymer having a Shore A hardness of from 20 to 50.

14. A device for maintaining an airway in a patient as claimed in claim 1 wherein the wall of the chamber includes a proximal wall portion, opposed side wall portions and a distal portion and the proximal portion of the mask that is adapted to collapse or compress extends from the proximal wall portion of the wall of the chamber and at least partly along the opposed side walls of the chamber.

15. A device for maintaining an airway in a patient as claimed in claim 1 wherein the mask comprises the region of relatively high strength or stiffness, the proximal portion that is adapted to collapse or compress and a dorsal region of relatively high strength or stiffness, the region of relatively high strength or stiffness being continuous with or joining with the dorsal region of relatively high strength or stiffness at a position located distally of a distal part of the proximal portion that is adapted to collapse or compress.

16. A device for maintaining an airway in a patient as claimed in claim 1 wherein the proximal portion that is adapted to collapse or compress comprises a region having a lesser wall thickness than a wall thickness of adjacent regions.

17. A device for maintaining an airway in a patient, the device comprising a mask having a portion that forms a seal with the larynx when the mask is positioned in the laryngo pharynx to thereby prevent ingress of extraneous fluids into the larynx, and an airway tube connected to or formed with the mask for passing gas to the larynx when the mask is properly inserted into the laryngo pharynx, the mask includes a chamber having an opening in fluid communication with the airway tube, the chamber including an outlet through which pressurised gases are supplied to the patient, the chamber including a wall having a wall portion extending from a ventral side of the mask towards a dorsal side of the mask, the wall of the chamber includes a proximal wall portion, opposed side wall portions and a distal portion, wherein the mask includes a proximal portion adapted to collapse or compress so that a proximal ventral part of the mask can move relatively towards a dorsal part of the device during insertion of the mask, wherein the proximal portion that is adapted to collapse or compress is shaped to facilitate collapsing or compressing, wherein the proximal portion of the mask, when viewed in cross section, has a first region extending inwardly into the chamber, a second region depending ventrally from the first region, the second region extending outwardly from the first region, whereby the second region can flex outwardly relative to the first region to thereby facilitate collapsing or compressing.

18. A device for maintaining an airway in a patient as claimed in claim 17 wherein the mask includes a soft, flexible portion that contacts tissues surrounding the laryngeal opening when the device is inserted into a patient, the soft, flexible portion being arranged whereby application of pressurised gas to the airway tube urges the soft, flexible portion into contact with the tissues surrounding the laryngeal opening or the pharyngeal wall.

19. A device as claimed in claim 17 further comprising a third region extending ventrally and inwardly from the second region, such the third region can flex inwardly relative to a ventral part of the second region to thereby facilitate collapsing or compressing.

\* \* \* \* \*